US009599810B2

(12) United States Patent
Matsui et al.

(10) Patent No.: US 9,599,810 B2
(45) Date of Patent: Mar. 21, 2017

(54) STEREOSCOPIC ENDOSCOPE SYSTEM

(71) Applicant: OLYMPUS CORPORATION, Tokyo (JP)

(72) Inventors: Toshihiro Matsui, Fussa (JP); Takanori Ushijima, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/159,223

(22) Filed: May 19, 2016

(65) Prior Publication Data
US 2016/0259159 A1 Sep. 8, 2016

Related U.S. Application Data

(63) Continuation of application No. PCT/JP2014/078570, filed on Oct. 28, 2014.

(30) Foreign Application Priority Data

Dec. 5, 2013 (JP) .................................. 2013-252144

(51) Int. Cl.
*G02B 23/24* (2006.01)
*A61B 1/00* (2006.01)
(Continued)

(52) U.S. Cl.
CPC ...... *G02B 23/2484* (2013.01); *A61B 1/00057* (2013.01); *A61B 1/00163* (2013.01);
(Continued)

(58) Field of Classification Search
CPC ............ G02B 23/2484; G02B 23/2423; G02B 23/2461; G02B 23/2415; G02B 23/26;
(Continued)

(56) References Cited

U.S. PATENT DOCUMENTS 5,577,991 A * 11/1996 Akui .................... A61B 1/0005
348/45
6,464,633 B1 * 10/2002 Hosoda ................ A61B 1/0638
348/68
(Continued)

FOREIGN PATENT DOCUMENTS

EP 2474262 B1 7/2013
EP 2768226 A1 8/2014
(Continued)

OTHER PUBLICATIONS

International Search Report dated Feb. 10, 2015 issued in PCT/JP2014/078570.
(Continued)

*Primary Examiner* — Sath V Perungavoor
*Assistant Examiner* — Howard D Brown, Jr.
(74) *Attorney, Agent, or Firm* — Scully, Scott, Murphy & Presser, PC

(57) ABSTRACT

A stereoscopic endoscope system includes: first and second image pickup sections including first and second image pickup devices, respectively, arranged on an endoscope distal end portion and configured to acquire a common subject; a reference member integrally provided on the endoscope distal end portion and serving as a reference in adjusting the first and second image pickup sections such that images are picked up in first and second image pickup ranges that can be picked up by the first and second image pickup devices, respectively; and an adjustment section configured to adjust the image picked up by at least one of the image pickup sections to generate substantially horizontally symmetrical images when the first image and the second image obtained by picking up the images of the reference member by the first and second image pickup
(Continued)

devices, respectively, are displayed as left and right images on a display apparatus.

13 Claims, 17 Drawing Sheets

(51) Int. Cl.
G02B 23/26 (2006.01)
H04N 13/02 (2006.01)
A61B 1/045 (2006.01)
A61B 1/05 (2006.01)
H04N 5/225 (2006.01)

(52) U.S. Cl.
CPC .......... *A61B 1/00193* (2013.01); *A61B 1/045* (2013.01); *A61B 1/05* (2013.01); *G02B 23/2415* (2013.01); *G02B 23/2423* (2013.01); *G02B 23/2461* (2013.01); *G02B 23/26* (2013.01); *H04N 13/0239* (2013.01); *H04N 13/0296* (2013.01); *H04N 2005/2255* (2013.01)

(58) Field of Classification Search
CPC ....... A61B 1/00163; A61B 1/045; A61B 1/05; A61B 1/00193; A61B 1/00057; H04N 13/0296; H04N 13/0239; H04N 2005/2255
See application file for complete search history.

(56) References Cited

U.S. PATENT DOCUMENTS

| | | | |
|---|---|---|---|
| 7,170,677 B1* | 1/2007 | Bendall | A61B 1/0005 348/49 |
| 9,456,735 B2* | 10/2016 | Hrayr | A61B 1/00183 |
| 2001/0012053 A1* | 8/2001 | Nakamura | A61B 1/00193 348/45 |
| 2003/0060679 A1* | 3/2003 | Murata | A61B 1/00048 600/111 |
| 2012/0162369 A1* | 6/2012 | Ishikawa | A61B 1/00096 348/45 |
| 2013/0217965 A1* | 8/2013 | Sasamoto | G02B 7/08 600/109 |
| 2014/0218479 A1* | 8/2014 | Nishimura | G02B 23/2415 348/46 |

FOREIGN PATENT DOCUMENTS

| | | |
|---|---|---|
| JP | H06-059196 A | 3/1994 |
| JP | H08-126606 A | 5/1996 |
| JP | 2003-009185 A | 1/2003 |
| JP | 2007-044153 A | 2/2007 |
| JP | 2013-090035 A | 5/2013 |
| WO | WO 2012/005054 A1 | 1/2012 |
| WO | WO 2013/054891 A1 | 4/2013 |

OTHER PUBLICATIONS

Japanese Office Action dated Oct. 13, 2015 issued in JP 2015-533365.

* cited by examiner

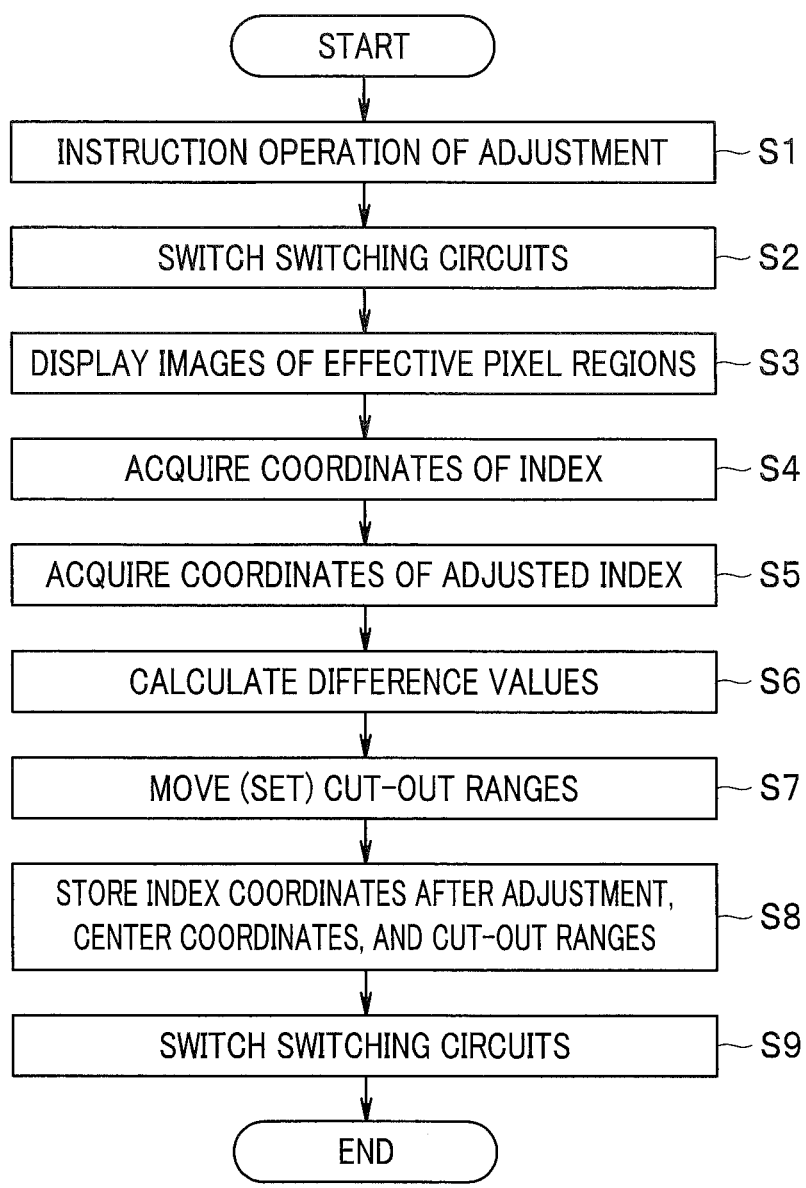

STEREOSCOPIC ENDOSCOPE SYSTEM

CROSS REFERENCE TO RELATED APPLICATION

This application is a continuation application of PCT/JP2014/078570 filed on Oct. 28, 2014 and claims benefit of Japanese Application No. 2013-252144 filed in Japan on Dec. 5, 2013, the entire contents of which are incorporated herein by this reference.

BACKGROUND OF INVENTION

1. Field of the Invention

The present invention relates to a stereoscopic endoscope system including left and right image pickup sections.

2. Description of the Related Art

In recent years, endoscopes have been widely used in a medical field and the like. A stereoscopic endoscope system using a stereoscopic endoscope is adopted in some cases to three-dimensionally observe a site to be operated or the like. In general, the stereoscopic endoscope includes a pair of left and right image pickup sections (or image pickup units). The left and right image pickup sections acquire parallax left and right pickup images of a subject (object), such as a site to be operated, and display the left and right images on a display apparatus through a signal processing apparatus. An operator uses polarization glasses or the like to three-dimensionally view the left and right images displayed on the display apparatus.

The left and right image pickup sections are set in a horizontally symmetrical state just after the manufacture of the stereoscopic endoscope and are set (adjusted) such that center positions of the left and right images respectively picked up by the left and right image pickup sections coincide to allow picking up images in a horizontally symmetrical image pickup state. However, degradation or the like of components included in the left and right image pickup sections due to repeated use generates a deviation from the horizontally symmetrical image pickup state, such as a deviation of the center positions.

Therefore, for example, Japanese Patent Application Laid-Open Publication No. 6-59196 discloses a configuration including adjustment means, in which a calibration tool as a reference of calibration is attached to a distal end portion of an insertion portion of a stereoscopic endoscope, reference images in which a distance from a distal end surface formed on an inner surface of the calibration tool is set to about several 10 mm are formed in left and right CCDs arranged at left and right image formation positions through left and right optical systems, respectively, and a relative position between the optical system and the CCDs is adjusted such that positions of images in the centers of fields of view in observation images picked up by the two CCDs coincide.

SUMMARY OF THE INVENTION

An aspect of the present invention provides a stereoscopic endoscope system including: a first image pickup section provided on an endoscope distal end portion, having a first field of view direction, and including a first objective optical system and a first image pickup device configured to acquire a first image of a subject; a second image pickup section provided on the endoscope distal end portion separately from the first image pickup section in a horizontal direction, having a second field of view direction, and including a second objective optical system and a second image pickup device configured to acquire a second image of the subject; a reference member integrally provided on the endoscope distal end portion and serving as a reference in adjusting the first and second image pickup sections such that images of at least a distal end side are picked up in first and second image pickup ranges that can be picked up by the first and second image pickup devices, respectively; and an adjustment section configured to adjust the image picked up by at least one of the image pickup sections or configured to adjust the one of the image pickup sections to generate substantially horizontally symmetrical images when the first image and the second image obtained by picking up the images of the reference member by the first and second image pickup devices, respectively, are displayed as left and right images in a display region of a display apparatus.

BRIEF DESCRIPTION OF THE DRAWINGS

FIG. 5 is a flowchart showing a procedure of an adjustment process according to the first embodiment;

DETAILED DESCRIPTION OF THE PREFERRED EMBODIMENT(S)

Hereinafter, embodiments of the present invention will be described with reference to the drawings.

First Embodiment

Figure 1:
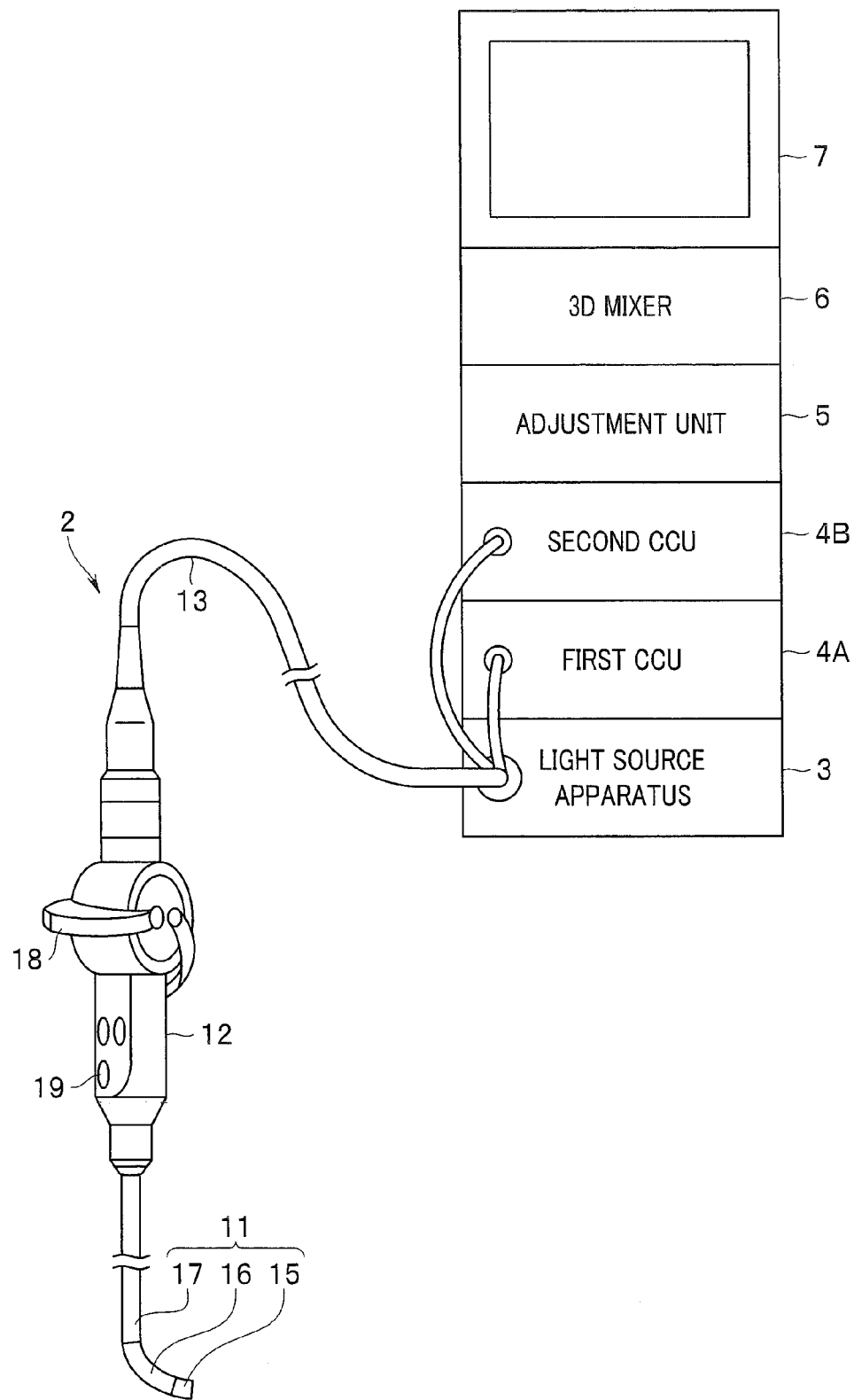
FIG. 1 is a diagram showing an overall configuration of a stereoscopic endoscope system according to a first embodiment of the present invention.

As shown in FIG. 1, a stereoscopic endoscope system 1 of a first embodiment of the present invention includes: a stereoscopic endoscope 2 configured to perform three-dimensional observation; a light source apparatus 3 configured to supply illuminating light to the stereoscopic endoscope 2; a first camera control unit (also called first CCU or simply CCU) 4A and a second CCU (also simply called CCU) 4B as signal processing apparatuses (or image processing apparatuses) configured to execute image processing for two image pickup sections provided on the stereoscopic endoscope 2; an adjustment unit 5 configured to execute image processing for adjusting a deviation or the like of a center position; a 3D mixer 6 configured to generate an image signal for three-dimensional view; and a 3D monitor 7 configured to display a three-dimensional image (3D image) to allow three-dimensional view.

The stereoscopic endoscope 2 includes: an elongated insertion portion 11; an operation portion 12 provided on a rear end (proximal end) of the insertion portion 11 and grasped and operated by a user such as an operator; and a universal cable 13 extended from the operation portion 12. A light guide connector at an end portion of the universal cable 13 is detachably connected to the light source apparatus 3.

The insertion portion 11 includes: a distal end portion 15 (as an endoscope distal end portion) provided at a distal end of the insertion portion 11; a bending portion 16 provided at a rear end of the distal end portion 15; and a rigid portion 17 with rigidity that is extended from a rear end of the bending portion 16 to the operation portion 12.

The operation portion 12 includes a grasping portion grasped by the user and is provided with a bending operation knob 18 and operation switches 19 for bending operation of the bending portion 16, at positions that allow operation by fingers of the hand grasping the grasping portion.

Figure 2A:
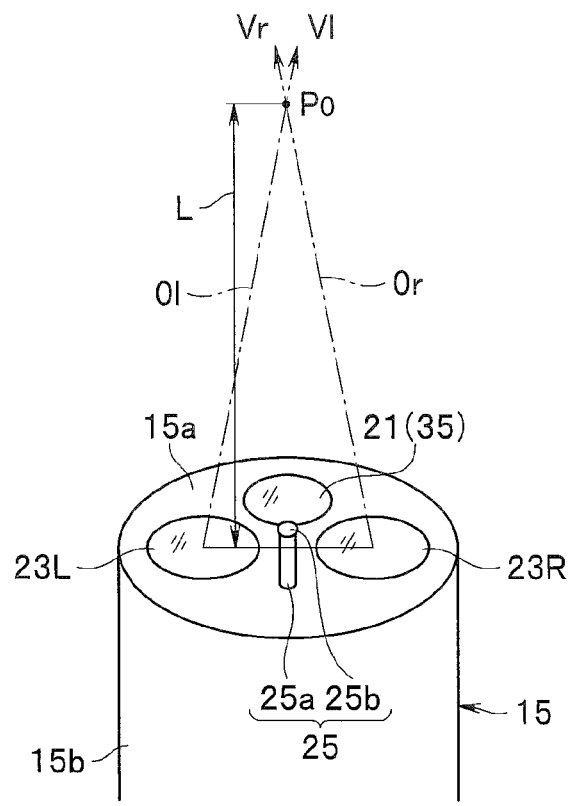
FIG. 2A is a perspective view showing a distal end portion of an insertion portion of a stereoscopic endoscope provided with a reference member.

FIG. 2A shows a perspective view of the distal end portion 15 of the insertion portion 11 of the stereoscopic endoscope 2. As shown in FIG. 2A, the distal end portion 15 is provided with: an illumination window 21 for emitting illuminating light; and left and right observation windows adjacent to the illumination window 21. Objective optical systems 23L and 23R forming a pair of left and right image pickup sections (see FIG. 3) 22L and 22R, respectively, are attached to the left and right observation windows, separately in a horizontal direction.

Figure 3:
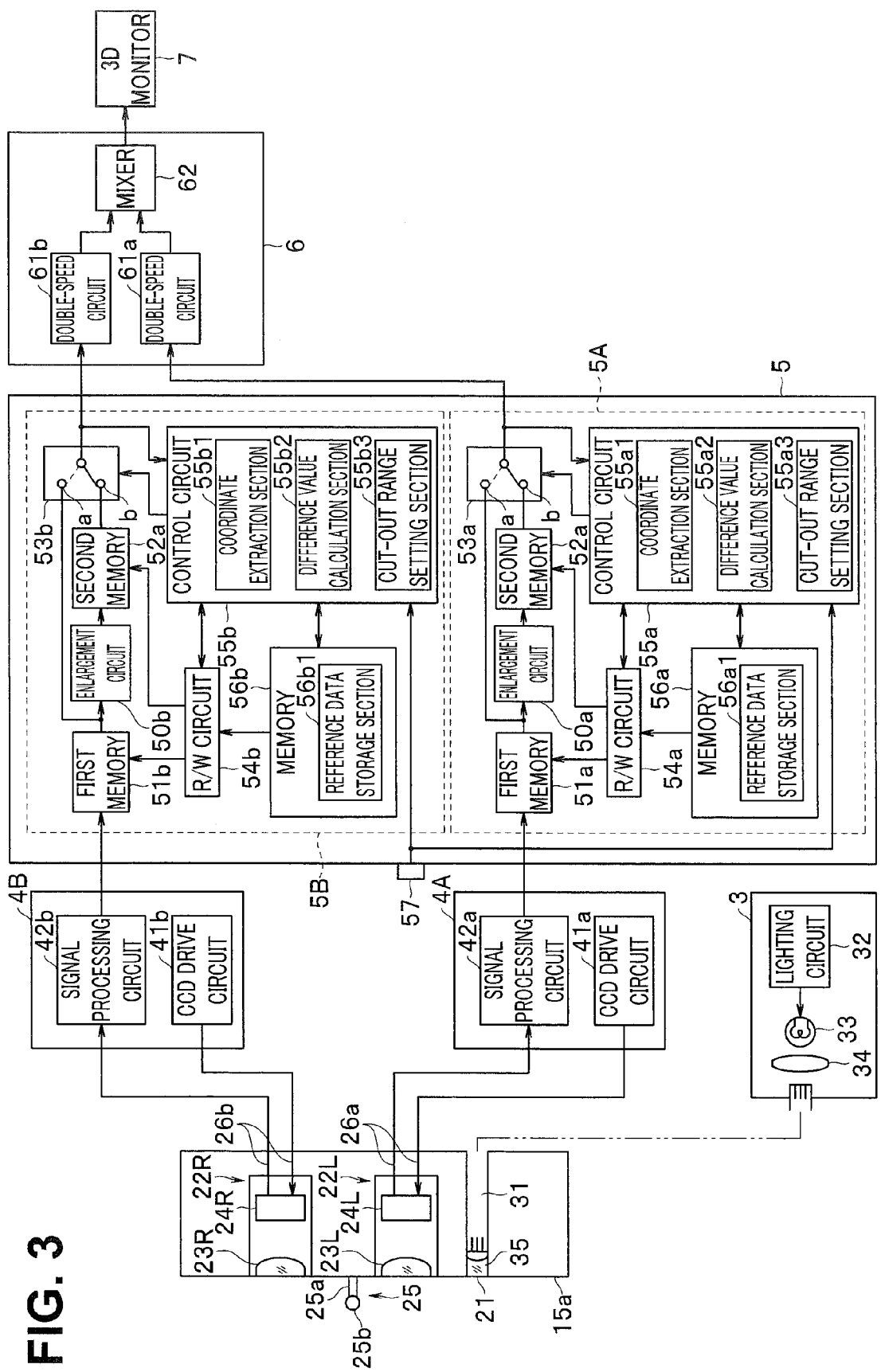
FIG. 3 is a diagram showing a schematic configuration of the stereoscopic endoscope, a light source apparatus, CCUs, an adjustment unit, and a 3D mixer in FIG. 1.

As shown in FIG. 3, the image pickup section 22L is configured to include: the objective optical system 23L; and a charge coupled device (abbreviated as CCD) 24L as an image pickup device arranged at an image formation position of the objective optical system 23L.

Similarly, the image pickup section 22R is configured to include: the objective optical system 23R; and a CCD 24R as an image pickup device arranged at an image formation position of the objective optical system 23R. Note that the image pickup device is not limited to the CCD, and a CMOS imager or the like may also be used.

As shown in FIG. 2A, an index member 25 forming a reference member is provided to protrude from a distal end surface 15a, at a symmetrical position with respect to the left and right image pickup sections 22L and 22R in the present embodiment. The index member 25 includes: an axis portion 25a in a columnar shape, in which a proximal end is fixed to the distal end surface 15a of the distal end portion 15; and an index 25b in, for example, a spherical shape provided at a distal end of the axis portion 25a.

In the example of FIG. 2A, a middle point of a line segment connecting both optical axes Ol and Or of the both objective optical systems 23L and 23R on the distal end surface 15a is set as a reference point, and the index member 25 is provided to protrude perpendicularly to the distal end surface 15a from the distal end surface 15a, at a position on a perpendicular line perpendicular to the line segment. When the left and right image pickup sections 22L and 22R arranged at horizontally symmetrical positions relative to the middle point have same characteristics, the both image pickup sections 22L and 22R pick up images of the index member 25 at horizontally symmetrical positions and pick up the images under equal conditions in relation to a direction perpendicular to the horizontal direction.

Figure 2B:
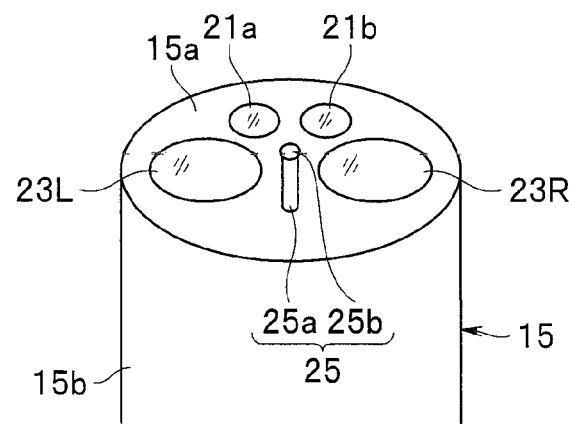
FIG. 2B is a perspective view showing the distal end portion of the insertion portion of the stereoscopic endoscope provided with the reference member when two illumination windows are included.

Note that although FIG. 2A illustrates a case in which one illumination window 21 is provided, two illumination windows 21a and 21b may be provided as shown in FIG. 2B. In a case of the two illumination windows 21a and 21b, one light guide 31 is branched into two light guides in the stereoscopic endoscope 2, and distal ends of the two light guides are fixed to the illumination windows 21a and 21b. An illumination lens 35 described later is attached to the illumination window 21 through a lens frame. In the case of the two illumination windows 21a and 21b, the illumination lens 35 is also attached to each window.

Figure 8:
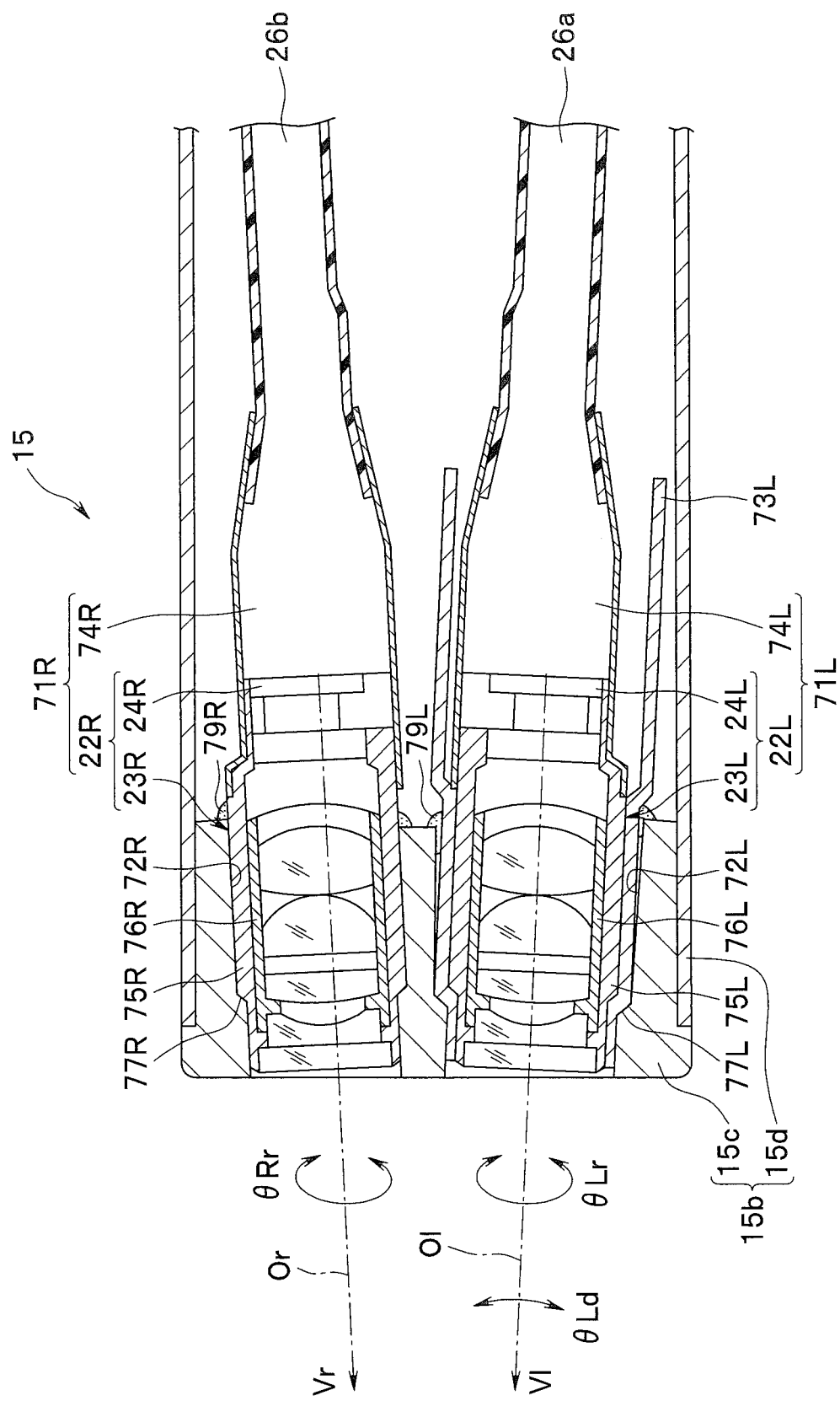
FIG. 8 is a cross-sectional view showing a configuration of the distal end portion of the stereoscopic endoscope according to a third modification of the first embodiment.

The left and right image pickup sections 22L and 22R are fixed into respective through holes for image pickup section attachment provided on a distal end member 15b included in the distal end portion 15, along a bending direction on the left and right of the bending portion 16 (on a rear end side of the distal end portion 15). An example of a more detailed structure of the image pickup sections 22L and 22R includes a structure as shown in FIG. 8 described later. Note that the distal end member 15b includes: a distal end portion main body (or support member) 15c in a columnar shape provided with through holes 72L and 72R; and a distal end cylindrical body 15d in a cylindrical shape, in which a distal end is fixed to the distal end portion main body 15c (see FIG. 8).

The image pickup sections 22L and 22R include: the left and right objective optical systems 23L and 23R with mutually uniform optical characteristics; and the left and right CCDs 24L and 24R adjusted such that image pickup surfaces are arranged at the image formation positions of the left and right objective optical systems 23L and 23R. The image pickup sections 22L and 22R are adjusted in respective two through holes provided separately in the horizontal direction in the distal end member 15b and are attached to form a horizontally symmetrical image pickup state at the middle point.

In the stereoscopic endoscope 2, the image pickup sections 22L and 22R are adjusted and attached in advance such that field of view directions Vl and Vr along directions of the respective optical axes Ol and Or of the both image pickup sections 22L and 22R (objective optical systems 23L and 23R included in the both image pickup sections 22L and 22R) are horizontally symmetrical (in a plane including the both optical axes Ol and Or) at manufacturing (or before factory shipment), and the both optical axes Ol and Or intersect at a point P0 at a predetermined distance L from the distal end surface 15a (from the middle point of the line segment connecting the both optical axes Ol and Or on the distal end surface 15a).

In FIG. 2A, dashed lines indicate the optical axes Ol and Or in the state adjusted in advance (that is, adjusted state). The objective optical systems 23L and 23R form images of a position of an object (subject) along the optical axes Ol and Or, at center positions of image pickup ranges on the image pickup surfaces of the CCDs 24L and 24R, respectively. The CCDs 24L and 24R photoelectrically convert (pick up) the images. As described later, when center positions (coordinates (Xl0, Yl0) and (Xr0, Yr0) of the center positions) of effective pixel regions 43La and 43Ra that form the image pickup ranges of the CCDs 24L and 24R are displayed as left and right images on a display region 7a of a display surface of the 3D monitor 7, the center positions coincide with a center position of the display region 7a as shown in FIG. 4C. Note that the entire display surface of the 3D monitor 7 may be set in the display region 7a, or part of the region in the display surface may be set for the display region 7a as an image display region.

As shown in FIG. 2A, the index member 25 passes through, for example, the middle point of the line segment connecting the both optical axes Ol and Or on the distal end surface 15a and protrudes to a front side perpendicular to the distal end surface 15a from a position on a line perpendicular to the line segment. A length (protruding height) of the axis portion 25a is set such that the index 25b is within the ranges of field of view of the both image pickup sections 22L and 22R (image pickup ranges of the CCDs 24L and 24R). The height from the distal end surface 15a to the index 25b can be set to, for example, several mm to about 1 cm or less according to characteristics of the objective optical systems 23L and 23R, such as view angles.

FIG. 3 shows a schematic configuration of the stereoscopic endoscope 2, the light source apparatus 3, the CCUs 4A and 4B, the adjustment unit 5, and the 3D mixer 6. As shown in FIG. 3, a rear end of (light guide connector of) the light guide 31 inserted into the stereoscopic endoscope 2 is connected to the light source apparatus 3. The light source apparatus 3 includes: a lighting circuit 32; a light source lamp 33 lit up by a lighting source of the lighting circuit 32; and a light collecting lens 34 configured to collect illuminating light emitted by the light source lamp 33 to cause the light to enter the rear end of the light guide 31.

The light source lamp 33 is formed by, for example, a xenon lamp and generates white light. Note that a light emitting diode or the like configured to generate white light may be used as the light source lamp 33. The illuminating light entering the rear end of the light guide 31 is emitted from the illumination window 21 of the distal end portion 15 of the insertion portion 11 and emitted to enlarge through the illumination lens 35. The illuminating light is emitted to cover the ranges of field of view of the both image pickup sections 22L and 22R.

The CCDs 24L and 24R are connected to the CCUs 4A and 4B, respectively, through cables 26a and 26b inserted into the stereoscopic endoscope 2. Note that in FIG. 1, the universal cable 13 through which the cables 26a and 26b are inserted is connected to connection cables extended from light guide connectors, and signal connectors of end portions of the connection cables are detachably connected to the CCUs 4A and 4B, respectively.

The CCUs 4A and 4B include: CCD drive circuits 41a and 41b configured to generate CCD drive signals for driving the CCDs 24L and 24R, respectively; and signal processing circuits 42a and 42b configured to apply signal processing to image signals picked up in the image pickup ranges on the image pickup surfaces of the CCDs 24L and 24R by applying the CCD drive signals to generate video signals (image signals) to be displayed on the monitor.

Figure 4A:
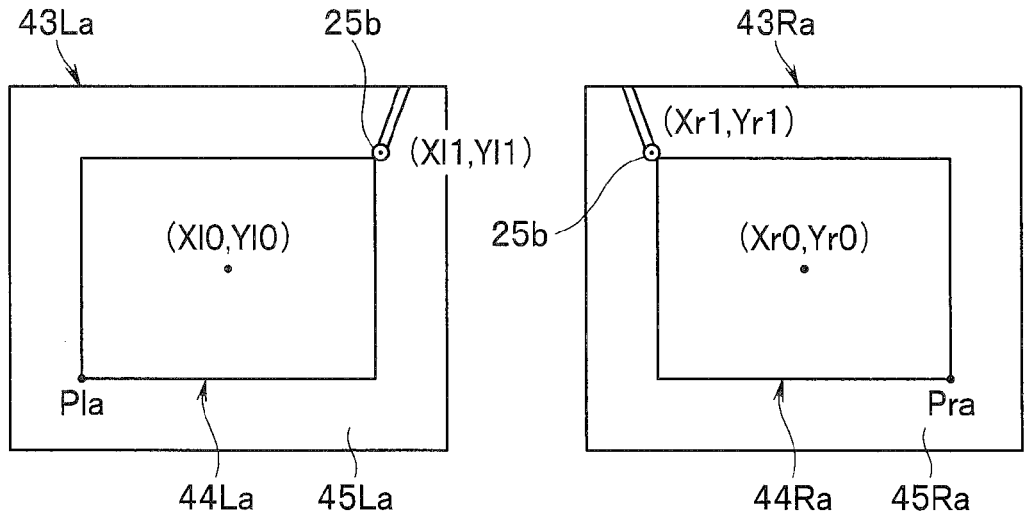
FIG. 4A is a diagram showing effective pixel regions of CCDs as image pickup devices and cut-out ranges set in the effective pixel regions.

Note that the image pickup ranges on the image pickup surfaces of the CCDs 24L and 24R are formed by the effective pixel regions 43La and 43Ra for performing photoelectric conversion (of the optical images formed by the objective optical systems 23L and 23R) and outputting electrical signals of the pickup images as shown in FIG. 4A.

As shown in FIG. 3, the CCD 24L is electrically connected to the CCU 4A, and the CCD 24R is electrically connected to the CCU 4B. Therefore, the signal processing circuit 42a generates a left image signal picked up by the left image pickup section 22L, and the signal processing circuit 42b generates a right image signal picked up by the right image pickup section 22R.

The left and right image signals generated by the signal processing circuits 42a and 42b are inputted to adjustment circuit units 5A and 5B, respectively, included in the adjustment unit 5.

Only the inputted image signals are different in the adjustment circuit units 5A and 5B, and the adjustment circuit units 5A and 5B have a same configuration, thereby having a same adjustment function. Therefore, the configuration of the adjustment circuit unit 5A of the adjustment circuit units 5A and 5B will be described below.

The left image signal generated by the signal processing circuit 42a is stored (or written) in a first memory 51a in the adjustment circuit unit 5A, and the left image signal stored in the first memory 51a is read and slightly enlarged by an enlargement circuit 50a. The left image signal is then stored in a second memory 52a and outputted to the 3D mixer 6 through a switching circuit 53a.

The enlargement circuit 50a applies an enlargement process to the left image stored in the first memory 51a to display, on the entire display region 7a of the 3D monitor 7, the image picked up in a cut-out range 44La on a center side of the effective pixel region 43La shown in FIG. 4A. A magnification in the enlargement process can be brought into line with a size ratio in a horizontal (lateral) direction or a perpendicular (longitudinal) direction in the cut-out range and the effective pixel region.

Note that when the left image signal generated by the signal processing circuit 42a is an analog image signal, an A/D conversion circuit not shown converts the analog image signal to a digital image signal and stores the digital image signal in the first memory 51a.

A read/write circuit 54a performs writing (write) and reading (read) of the image signal to and from the first memory 51a and the second memory 52a. A control circuit 55a controls operation of read/write of the read/write circuit 54a.

The second memory 52a stores an image (also called a cut-out image) in the cut-out range 44La on the center side obtained by removing an effective pixel region 45La on a peripheral side from the effective pixel region 43La. Therefore, the second memory 52a forms a cut-out image generation section (or a cut-out image storage section) configured to generate or store the cut-out image. Note that it can also be defined that the cut-out image generation section (cut-out image generation circuit) configured to generate the cut-out image includes the first memory 51a, the enlargement circuit 50a, the second memory 52a, and the read/write circuit 54a.

The image signal picked up in the (entire) effective pixel region 43La outputted from the first memory 51a is applied to a contact point a of the switching circuit 53a, and the image signal picked up in the cut-out range 44La outputted from the second memory 52a is applied to another contact point b.

In a normal use state, the switching circuit 53a is set to select the contact point b. In this way, the image signal picked up in the cut-out range 44La is outputted toward the 3D mixer 6 side as an image signal for normal display, and the image signal picked up in the cut-out range 44La is displayed on the 3D monitor 7 as a left image in a 3D image.

On the other hand, when the user operates an adjustment instruction switch 57, a signal of adjustment instruction is inputted to the control circuit 55a (also inputted to a control circuit 55b). When the signal of adjustment instruction is inputted, the control circuit 55a switches the switching circuit 53a to select the contact point a, and the image signal picked up in the effective pixel region 43La is outputted toward the 3D mixer 6 side.

The image signal picked up in the effective pixel region 43La is displayed on the 3D monitor 7 as the left image in the 3D image. In this case, the image signal picked up (photoelectrically converted) in the effective pixel region 43La is also inputted to the control circuit 55a, and the control circuit 55a has a function of executing an adjustment process as described below.

The control circuit 55a is formed by a central processing unit (abbreviated as CPU) or the like and functions as a coordinate extraction section (or a coordinate extraction circuit) 55a1 configured to extract coordinates (X12, Y12) of a two-dimensional position of the index 25b (center of the index 25b) in the image at the adjustment (image picked up in the effective pixel region 43La) when the image signal at the adjustment is inputted. As described, the image at the adjustment corresponds to the image obtained by photoelectrically converting the optical image formed in the effective pixel region 43La, and the coordinates (X12, Y12) of the image at the adjustment are the same as the coordinates of the pixel position in the effective pixel region 43La.

The adjustment circuit unit 5A includes a memory 56a connected to the control circuit 55a and configured to store data.

As shown in FIG. 4C, at the factory shipment for example, the memory 56a stores reference data that is data of reference coordinates that are coordinates (X11, Y11) and (Xr1, Yr1) of two-dimensional positions of the index 25b (center of the index 25b) when image of the index 25b is picked up in an adjusted state. In the adjusted state, the positions of the centers of the effective pixel regions 43La and 43Ra (both coordinates (X10, Y10) and (Xr0, Yr0) of the positions) are adjusted to coincide when image of the predetermined position P0 (see FIG. 2A) is picked up by the left and right image pickup sections 22L and 22R, and it is adjusted to eliminate deviations or inclinations (rotation deviations about the optical axes Ol and Or) in the vertical and horizontal directions (or azimuths) of the images between the both CCDs 24L and 24R.

Note that FIG. 4C shows an example in which the images of the effective pixel regions 43La and 43Ra are displayed on the display region 7a of the 3D monitor 7. Therefore, "7a=43La, 43Ra" indicates that the display region 7a is equivalent to the effective pixel regions 43La and 43Ra. In this case, the cut-out ranges 44La and 44Ra are displayed in the region 7b inside of the display region 7a. This is indicated by "7b=44La, 44Ra".

Figure 4B:
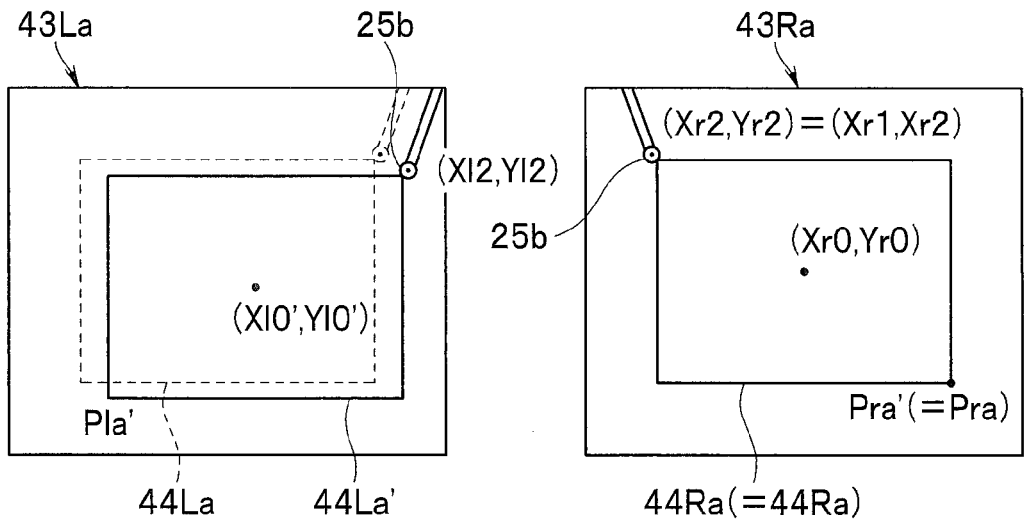
FIG. 4B is an explanatory view of operation of setting the cut-out ranges at adjustment.
Figure 4C:
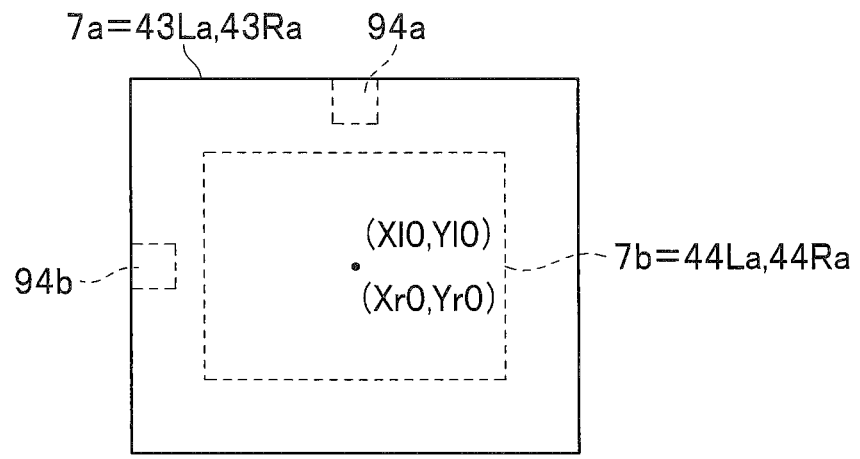
FIG. 4C is a diagram showing circumstances that center positions of the effective pixel regions coincide when displayed on a 3D monitor.
Figure 4D:
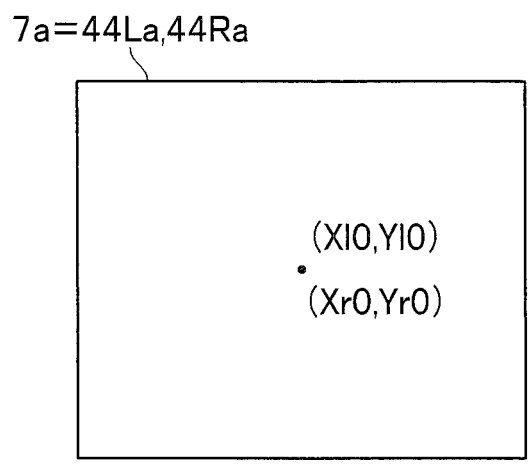
FIG. 4D is a diagram showing circumstances that the cut-out ranges on center sides of the effective pixel regions are displayed on an entire display surface of the 3D monitor.

On the other hand, when the image signals stored in the second memories 52a and 52b are displayed in the display regions 7a of the 3D monitor 7, the entire display region 7a is equivalent to the cut-out ranges 44La and 44Ra, and this is indicated by "7a=44La, 44Ra" as shown in FIG. 4D.

The memory 56a functions as a reference data storage section (or a reference data storage unit) 56a1 configured to store the reference data of the image pickup section 22L in the adjusted state adjusted in advance. Other than the reference data, data necessary to determine the cut-out range may also be stored in the memory 56a. More specifically, data (address information equivalent to the data) of coordinates of a position Pla used to determine the rectangular cut-out range 44La in FIG. 4A may be stored. Note that the case is not limited to the case in which the data of the coordinates of the position Pla is stored in the memory 56a in addition to the reference data, and information of a length of one side or two sides of the rectangular cut-out range may be stored as the data for determining the cut-out range 44La.

The read/write circuit 54a refers to the address information of the cut-out range stored in the memory 56a to write the image (data) of the cut-out range in the second memory 52 or to read the image from the second memory 52a. Note that the lateral (horizontal) direction and the longitudinal (perpendicular) direction in FIG. 4A correspond to X axis and Y axis directions.

The control circuit 55a calculates a difference value (X12−X11, Y12−Y11) between the coordinates (X12, Y12) of the index 25b extracted by the coordinate extraction section 55a1 in the image at the adjustment and the reference coordinates (X11, Y11) of the index 25b read from the memory 56a. That is, the control circuit 55a functions as a difference value calculation section (or difference value calculation circuit) 55a2 configured to calculate the difference value between the coordinates of the index 25b extracted by the coordinate extraction section 55a1 at the adjustment and the reference coordinates of the index 25b in the adjusted state adjusted in advance.

The control circuit 55a moves the cut-out range 44La based on the difference value (by an amount of the difference value) to set an adjusted new cut-out range 44La'. That is, the control circuit 55a functions as a cut-out range setting section (or cut-out range setting circuit) 55a3 configured to set a cut-out range adjusted to a position obtained by two-dimensionally shifting the cut-out range 44La by the amount of the difference value based on a calculation result of the difference value by the difference value calculation section 55a2.

The adjustment circuit unit 5B includes components with ○○b in place of ○○a of the first memory 51a, the enlargement circuit 50a, the second memory 52a, the switching circuit 53a, the read/write circuit 54a, the control circuit 55a, and the memory 56a in the adjustment circuit unit 5A. Only the inputted signal is different, and the components and the functions are the same. The description will not be repeated.

The output signals of the adjustment circuit units 5A and 5B are inputted to double-speed circuits 61a and 61b included in the 3D mixer 6, respectively. The signals are converted to double-speed left and right image signals in which a cycle of the signal of each frame is compressed to ½, and the signals are inputted to a mixer 62. The signals are mixed and converted to a 3D image signal. The 3D image signal is outputted to the 3D monitor 7, and the left and right images are, for example, alternately displayed on the display surface of the 3D monitor 7. The user, such as an operator, uses liquid crystal shutter glasses to three-dimensionally view the left and right images displayed on the 3D monitor 7. Note that the 3D monitor may be a polarization 3D monitor that allows three-dimensional view by displaying left and right polarized images corresponding to left and right polarization directions in polarization glasses.

The stereoscopic endoscope system 1 of the present embodiment includes: a first image pickup section (22L or 22R) provided on the distal end portion 15 as an endoscope distal end portion, having a first field of view direction, and including a first objective optical system and a first image pickup device configured to acquire a first image of a subject; a second image pickup section (22R or 22L) provided on the endoscope distal end portion separately from the first image pickup section in the horizontal direction, having a second field of view direction, and including a second objective optical system and a second image pickup device configured to acquire a second image of the subject; the index member 25 as a reference member integrally provided on the endoscope distal end portion and serving as a reference for adjusting the first and second image pickup sections such that images of at least a distal end side are picked up in first and second image pickup ranges that can be picked up by the first and second image pickup devices, respectively; and the adjustment unit 5 forming an adjustment section configured to adjust the image picked up by at least one of the image pickup sections to generate substantially horizontally symmetrical images when the first image and the second image obtained by picking up the images of the reference member by the first and second image pickup devices, respectively, are displayed as left and right images in a display region of a display apparatus.

Note that an adjustment section configured to adjust at least one of the image pickup sections to generate substantially horizontally symmetrical images when the first image and the second image obtained by picking up the images of the reference member by the first and second image pickup devices are displayed as left and right images in the display region of the display apparatus will be described later in FIG. 8.

Next, operation of the present embodiment will be described.

First, the attachment positions of the both image pickup sections 22L and 22R attached to the distal end portion 15 are adjusted to set the state in which the deviation of the center positions and the inclinations (rotations) of the optical axes Ol and Or are eliminated. In this state, the coordinates (Xl0, Yl0) and (Xr0, Yr0) at the center positions of the left and right images picked up in the image pickup ranges (effective pixel regions 43La and 43Ra) of the CCDs 24L and 24R are displayed to coincide at, for example, the center position in the display region 7a of the 3D monitor 7 as shown in FIG. 4C.

Furthermore, the images of the index 25b (of the index member 25) formed on the image pickup surfaces of the CCDs 24L and 24R are horizontally symmetrical to each other as in FIG. 4A.

The left and right coordinates (Xl1, Yl1) and (Xr1, Yr1) indicating the positions of the index 25b are horizontally symmetrical to each other with respect to the coordinates (Xl0, Yl0) and (Xr0, Yr0) of the center positions. In this state, the coordinates (Xl1, Yl1) and (Xr1, Yr1) serve as respective reference positions, and the rectangular cut-out ranges 44La and 44Ra are set. More specifically, the coordinates (Xl1, Yl1) and (Xr1, Yr1) serve as an upper right peak and an upper left peak that are boundary positions of the cut-out ranges, and the cut-out ranges 44La and 44Ra are set, respectively.

In this case, the coordinates (Xl1, Yl1) and (Xr1, Yr1) are on the boundary positions for determining the cut-out ranges 44La and 44Ra. As described below, the points Pla and Pra in FIG. 4A are also points for determining the cut-out ranges 44La and 44Ra.

When the images of the cut-out ranges 44La and 44Ra obtained by cutting out the regions of the center sides in the effective pixel regions 43La and 43Ra are displayed on the 3D monitor 7, the coordinates (Xl1, Yl1) and (Xr1, and Yr1) of the index 25b are boundary positions not displayed. The cut-out ranges 44La and 44Ra are set to display regions of normal images (signals) in the 3D monitor 7. That is, as shown in FIG. 4D, the left and right images picked up in the cut-out ranges 44La and 44Ra are displayed in the entire display region 7a (after enlargement process by the enlargement circuits 50a and 50b), and regions (peripheral side effective pixel regions indicated by 45La and 45Ra) including the index 25b outside of the cut-out ranges 44La and 44Ra are not displayed.

Figure 4E:
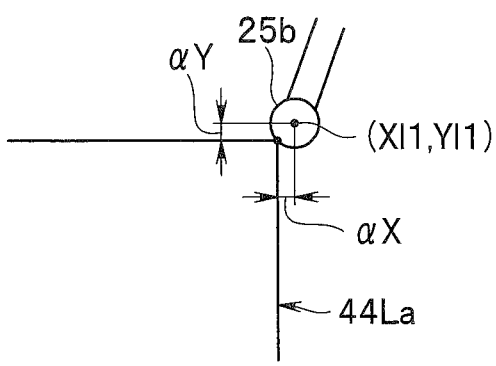
FIG. 4E is an explanatory view of a case in which a magnitude of a size of an index is taken into account to set reference coordinates of the cut-out ranges.

Note that, if it is better to consider the size of the spherical shape of the index 25b instead of the point of the index 25b when the cut-out range 44La is to be set for example, a position on the sphere obtained by shifting the coordinates (Xl1, Yl1) of the position of the center by αX and αY may be set as the reference position of the index 25b for setting the cut-out range 44La as shown in FIG. 4E. The same applies to the cut-out range 44Ra.

The coordinates (Xl1, Yl1) and (Xr1, Yr1) are stored in the memories 56a and 56b, respectively, and are referenced in subsequent adjustment. Data for determining the sizes of the cut-out ranges 44La and 44Ra (for example, data of the coordinates of the points Pla and Pra in FIG. 4A) are also stored in the memories 56a and 56b. The coordinates of the point Pla are coordinates centrosymmetric with respect to the coordinates (Xl0, Yl0) of the center position, and similarly, the coordinates of the point Pra are coordinates centrosymmetric with respect to the coordinates (Xr0, Yr0) of the center position.

In the state that the both image pickup sections 22L and 22R are appropriately adjusted in this way, the operator as a user uses the stereoscopic endoscope 2 to perform a three-dimensional observation or an operation based on the three-dimensional observation. When the operator desires to check or adjust the image pickup state of the both image pickup sections 22L and 22R, the operator operates the adjustment instruction switch 57 as shown in step S1 of FIG. 5 and performs instruction operation of adjustment. Note that the adjustment instruction switch 57 may be operated in an initial state for performing adjustment of white balance and the like. The adjustment instruction switch 57 may also be operated in a state for picking up an image of a white object after the adjustment of the white balance.

As shown in step S2, the control circuits 55a and 55b switch the switching circuits 53a and 53b according to the instruction operation of adjustment. The contact point b is selected in a normal state, and the control circuits 55a and 55b switch the switching circuits 53a and 53b to select the contact point a instead of the contact point b.

When the switching circuits 53a and 53b are switched, the adjustment circuit units 5A and 5B output the image signals of the first memories 51a and 51b to the 3D monitor 7 as shown in step S3. In this case, the 3D monitor 7 displays the images picked up in the effective pixel regions 43La and 43Ra that are respective image pickup ranges of the CCDs 24L and 24R.

The image signals in this case are inputted to the control circuits 55a and 55b, respectively. In this case, the state of the image pickup in the respective effective pixel regions 43La and 43Ra of the CCDs 24L and 24R are the state shown in FIG. 4B. FIG. 4B shows a case in which the image pickup section 22L is slightly deviated from the adjusted state (at the factory shipment), and the other image pickup section 22R is not changed from the adjusted state.

Note that when the displacement from the adjusted state is small, the amount of displacement can be approximated by assuming that each position is simply shifted from the adjusted state. Therefore, in most cases, the center position can be approximated by assuming that the center position is shifted by δ when, for example, the reference position in the adjusted state is shifted by δ.

As shown in step S4, the control circuits 55a and 55b (coordinate extraction sections 55a1 and 55b1 of the control circuits 55a and 55b) acquire the data of the coordinates (X12, Y12) and (Xr2, Yr2) of the index 25b from the left and right image signals, respectively.

As shown in next step S5, the control circuits 55a and 55b read, as reference coordinates, the coordinates (X11, Y11) and (Xr1, Yr1) of the adjusted index 25b of FIG. 4A as reference data from the memories 56a and 56b and send the coordinates to the difference value calculation sections 55a2 and 55b2.

As shown in next step S6, the difference value calculation sections 55a2 and 55b2 of the control circuits 55a and 55b calculate difference values between current coordinates extracted by the coordinate extraction sections 55a1 and 55b1 and the reference coordinates. That is, the difference value calculation sections 55a2 and 55b2 calculate difference values (X12−X11, Y12−Y11) and (Xr2−Xr1, Yr2−Yr1). The calculated difference values (X12−X11, Y12−Y11) and (Xr2−Xr1, Yr2−Yr1) are sent to the cut-out range setting sections 55a3 and 55b3, respectively.

As shown in next step S7, the cut-out range setting sections 55a3 and 55b3 of the control circuits 55a and 55b move the adjusted cut-out ranges 44La and 44Ra by the difference values (X12−X11, Y12−Y11) and (Xr2−Xr1, Yr2−Yr1). In the case of FIG. 4B, the adjusted cut-out range 44La indicated by a dotted line is set to become the cut-out range 44La' indicated by a solid line.

In other words, the cut-out range setting sections 55a3 and 55b3 perform an adjustment of moving the cut-out ranges 44La and 44Ra (in the movement direction of the index and by the amount of movement) to bring the coordinates (X11, Y11) and (Xr1, Yr1) of the index 25b as reference positions into line with the coordinates (X12, Y12) and (Xr2, Yr2) of the extracted new index 25b. The coordinates (X10, Y10) of the adjusted center position shown in FIG. 4A are shifted by the amount equivalent to the difference value and moved to coordinates (X10', Y10') of the center position.

As shown in step S8, the control circuits 55a and 55b store, in the memories 56a and 56b, data of the coordinates of the new index 25b after the adjustment, the center coordinates, and the corresponding cut-out ranges 44La' and 44Ra' and end the adjustment process.

As shown in next step S9, the control circuits 55a and 55b switch the switching circuits 53a and 53b and end the process of FIG. 5. The operator then uses the stereoscopic endoscope 2 to perform three-dimensional observation or the like.

The process of performing the adjustment in the present embodiment is an adjustment process for the image picked up by at least one of the image pickup sections such that the both image pickup sections 22L and 22R generate substantially horizontally symmetrical images when images of the indexes 25b of the index members 25 horizontally symmetrically arranged for the both image pickup sections 22L and 22R are picked up by the both image pickup sections 22L and 22R, respectively, and displayed as left and right images in the display region 7a of the 3D monitor 7 as a display apparatus. Here, "generate substantially horizontally symmetrical images" indicates images generated in the cut-out ranges 44La' and 44Ra'.

After the execution of the adjustment process of FIG. 5, the image pickup state for picking up images in the cut-out ranges 44La' and 44Ra' by the both image pickup sections 22L and 22R can be set to an image pickup state close to the adjusted state at the factory shipment. That is, when the images of the point P0 in the object (or subject) at the predetermined distance L from the distal end surface 15a are picked up as shown in FIG. 2A, the images of the point P0 can be picked up near the center positions of the left and right cut-out ranges 44La' and 44Ra'.

In this case, the center positions of the left and right cut-out ranges 44La' and 44Ra' are center positions of normal display regions for displaying a normal image (image for three-dimensional view). Therefore, a state eliminating the deviation of the center positions can be set. Even if the coordinates (X11, Y11) and (Xr1, Yr1) of the index 25b are displaced due to an effect of secular change or the like, each position in the effective image pickup regions 43La and 43Ra can be approximated by assuming that the position is displaced by the same amount of displacement when the amount of displacement is small. Therefore, an amount of rotational displacement around the optical axes Ol and Or can be ignored.

That is, when the amount of displacement is small, the amount of displacement is a translational move, and the adjustment of the amount of difference value described above can adjust the image pickup state of the both image pickup sections 22L and 22R to generate substantially horizontally symmetrical images. More specifically, the image pickup state for displaying the respective images picked up in the cut-out ranges 44La' and 44Ra' by the both image pickup sections 22L and 22R as left and right images in the display region 7a of the 3D monitor 7 can be set to a state substantially equivalent to the image pickup state for picking up the images by the horizontally symmetrically set both image pickup sections 22L and 22R in the adjusted state.

Therefore, according to the present embodiment, operation of attaching and detaching a reference member necessary for performing the adjustment can be eliminated, and images such as images picked up in the horizontally symmetrical image pickup state can be acquired. Therefore, when the user, such as an operator, three-dimensionally views the left and right images displayed on the 3D monitor 7 by left and right eyes, the user can observe the images in a state that the three-dimensional view of the images is easy, without deviation of the center positions and without inclination around the optical axes. As a result, the user can smoothly perform the operation or the like.

In the present embodiment, the user only operates the adjustment instruction switch 57, and the adjustment unit 5 automatically executes the adjustment process of the both image pickup sections 22L and 22R (cut-out ranges of the both image pickup sections 22L and 22R). Therefore, the burden of the user can be reduced, and the stereoscopic endoscope system 1 with a high operability (convenience) can be realized.

According to the present embodiment, the index member 25 is integrally provided on the distal end portion 15. Therefore, unlike in the conventional example, the operation of attaching the index member 25 at the adjustment and removing the index member 25 after the adjustment is not necessary, and the burden of the user, such as an operator, can be reduced. Furthermore, when the stereoscopic endoscope 2 is disinfected or sterilized, the index member 25 is also disinfected or sterilized at the same time. Therefore, there is no need to consider the disinfection, the sterilization, or the like of the index member 25 as a separate body, and the burden of the user, such as an operator, can be reduced.

Figure 6A:
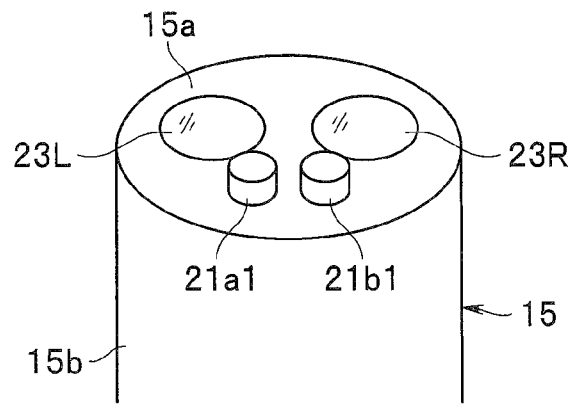
FIG. 6A is a perspective view showing a configuration of the distal end portion of the stereoscopic endoscope according to a first modification of the first embodiment.

Next, a first modification of the first embodiment will be described. In the first modification, for example, illumination lens frames 21a1 and 21b1 forming the illumination windows 21a and 21b are provided near the position of the index member 25 of FIG. 2B to provide the function of the index member 25. Respective illumination lenses (see FIG. 3) are attached to the inside of the illumination lens frames 21a1 and 21b1. FIG. 6A shows a perspective view of the vicinity of the distal end portion 15 in this case. Distal end sides of the illumination lens frames 21a1 and 21b1 protrude to the front side from the distal end surface 15a so that the illumination lens frames 21a1 and 21b1 are horizontally symmetrical with respect to the both image pickup sections 22L and 22R on the distal end surface 15a. The illumination lens frames 21a1 and 21b1 are integrally provided on the distal end member 15b to allow capturing the distal end sides in the image pickup ranges of the both image pickup sections 22L and 22R as shown in FIG. 6B.

Figure 6B:
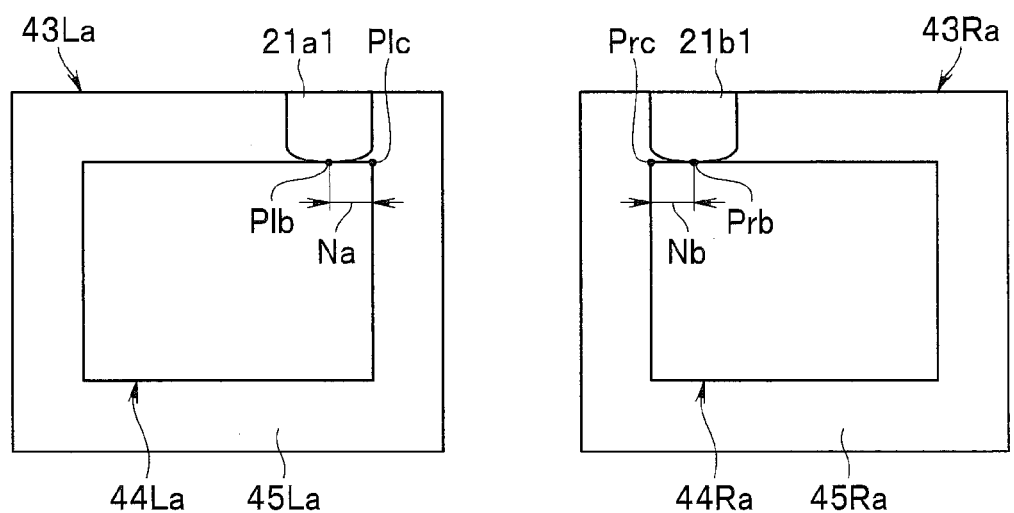
FIG. 6B is an explanatory view of circumstances of capturing and picking up images of the indexes in the effective pixel regions to set the cut-out ranges according to the first modification of the first embodiment.

FIG. 6B shows circumstances of picking up images of the illumination lens frames 21a1 and 21b1 by using the left and right effective pixel regions 43La and 43Ra forming the both image pickup ranges when the images are picked up by the both image pickup sections 22L and 22R in the adjusted state at the factory shipment in the case of the configuration.

As shown in FIG. 6B, the distal end sides of the illumination lens frames 21a1 and 21b1 are captured and the images are picked up in the left and right effective pixel regions 43La and 43Ra, respectively, and peaks Plb and Prb of contours at captured distal end side parts function as reference positions for determining the cut-out ranges 44La and 44Ra. In other words, positions near the contours at the distal end side parts whose images are picked up in the left and right effective pixel regions 43La and 43Ra are set as the reference positions equivalent to the function of the index 25b shown in FIG. 4A and the like. The cut-out ranges 44La and 44Ra are set to pass through the points Plb and Prb.

Note that in the example shown in FIG. 6B, the points Plb and Prb are not reference positions that are peaks of the rectangular cut-out ranges 44La and 44Ra, and positions (coordinate data of the positions) shifted by predetermined pixels Na and Nb in the horizontal direction are set to be the peaks of the cut-out ranges 44La and 44Ra. Obviously, the points Plb and Prb may be set to be the peaks of the rectangular cut-out ranges 44La and 44Ra.

In the present modification, the points Plb and Prb in contact with upper sides of the cut-out ranges 44La and 44Ra function as the reference positions for determining the cut-out ranges 44La and 44Ra. However, as described, coordinates of a point Plc shifted to the right side in the horizontal direction by the predetermined pixels Na from the point Plb are equivalent to the coordinates (Xl1, Yl1) of the first embodiment in the case of FIG. 6B. Similarly, coordinates of a point Prc shifted to the left side in the horizontal direction by the predetermined pixels Nb from the point Prb are equivalent to the coordinates (Xr1, Yr1) of the first embodiment in the case of FIG. 6B.

The rest is the same as in the first embodiment. The illumination lens frames 21a1 and 21b1 protruding from the distal end surface 15a are used as reference members, and the present modification has substantially the same effects as in the first embodiment.

According to the present modification, the illumination lens frames 21a1 and 21b1 are provided to protrude from the distal end surface 15a to provide the function of index members in a normal stereoscopic endoscope, and therefore, there is an advantage that the index member 25 necessary for the adjustment does not have to be newly provided. Note that the case is not limited to the case in which two illumination lens frames 21a1 and 21b1 are provided to protrude from the distal end surface 15a, and one illumination lens frame may be provided to protrude from the distal end surface 15a.

Figure 7A:
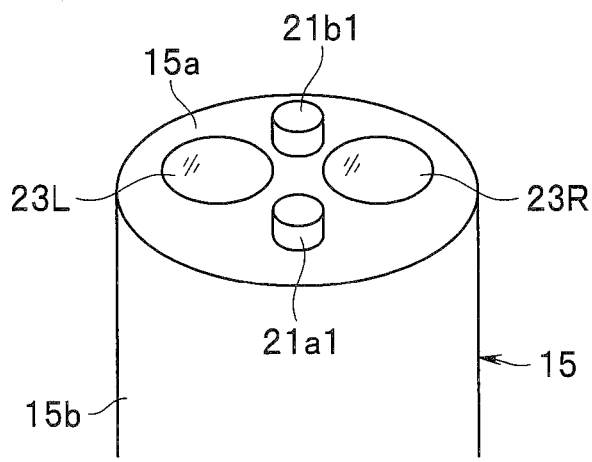
FIG. 7A is a perspective view showing a configuration of the distal end portion of the stereoscopic endoscope according to a second modification of the first embodiment.

Next, a second modification of the present embodiment will be described. In the present modification, the two illumination lens frames 21a1 and 21b1 are arranged in the vertical direction as shown in FIG. 7A, and the two illumination lens frames 21a1 and 21b1 are arranged vertically symmetrical with respect to the image pickup sections 22L and 22R separately arranged in the vertical direction. More specifically, the illumination lens frames 21a1 and 21b1 are arranged on positions at a same distance on a perpendicular line bisecting the line segment connecting the both optical axes Ol and Or (not shown in FIG. 7A) of the both image pickup sections 22L and 22R that are separate in the horizontal direction on the distal end surface 15a.

Figure 7B:
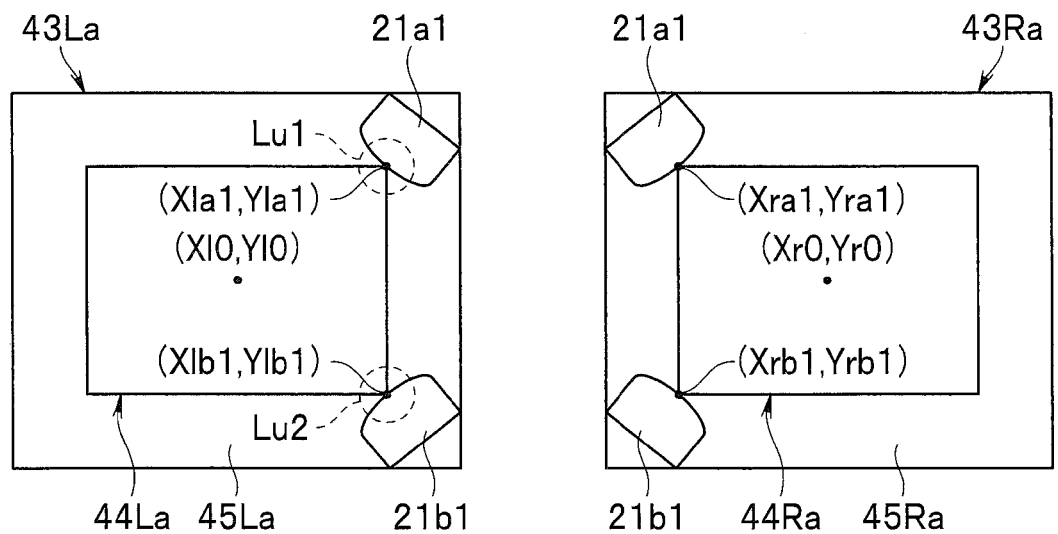
FIG. 7B is a diagram showing circumstances that the images of the indexes are picked up in advance in the effective pixel regions of the CCDs to set the cut-out ranges.

In the adjusted state adjusted in advance at the factory shipment or the like, the images of the illumination lens frames 21a1 and 21b1 are vertically symmetrically picked up in the effective pixel regions 43La and 43Ra as in FIG. 7B for example, and the images of the peaks of the contours at the distal end side parts of the illumination lens frames 21a1 and 21b1 picked up in the effective pixel regions 43La and 43Ra are set as the reference positions for determining two peaks of the cut-out ranges 44La and 44Ra.

In the effective pixel region 43La, coordinates (Xla1, Yla1) and (Xlb1, Ylb1) of the peaks of the contours at the distal end side parts of the illumination lens frames 21a1 and 21b1 serve as reference data for determining the two peaks of the rectangular cut-out range 44La. The rectangular cut-out range 44La is determined in which the coordinates (X10, Y10) of the center are a point of intersection of two diagonals, and two coordinates (Xla1, Yla1) and (Xlb1, Ylb1) on the two diagonals are the two peaks, respectively.

Similarly, coordinates (Xra1, Yra1) and (Xrb1, Yrb1) of the peaks of the contours at the distal end side parts of the illumination lens frames 21a1 and 21b1 serve as reference data for determining the cut-out range 44Ra in the effective pixel region 43Ra.

The rectangular cut-out range 44Ra is determined in which coordinates (Xr0, Yr0) of the center are a point of intersection of two diagonals, and two coordinates (Xra1, Yra1) and (Xrb1, Yrb1) on the two diagonals are the two peaks, respectively.

Figure 7C:
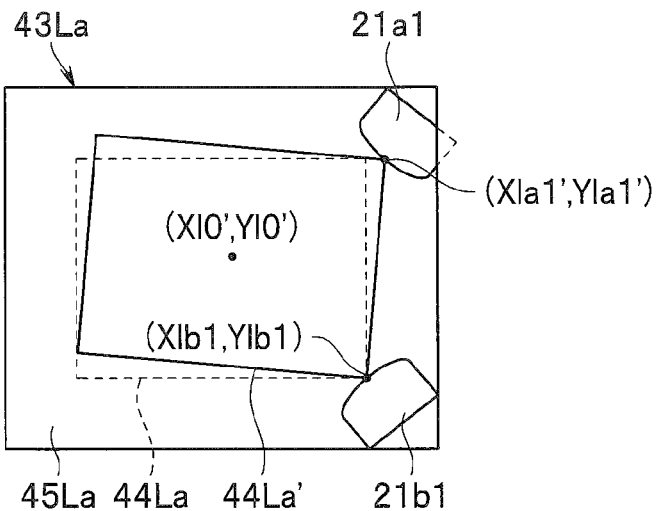
FIG. 7C is a diagram showing circumstances of adjusting the cut-out range of the left CCD based on the positions of the indexes.

In the present modification, it is assumed for example that the image pickup section 22L side is changed as shown for example in FIG. 7C from the adjusted state at the factory shipment, due to a long time use. FIG. 7C shows a case in which, for example, the position of the coordinates (Xlb1, Ylb1) does not change, and the other coordinates (Xla1, Yla1) are changed.

In this case, the processing procedure shown in FIG. 5 can also adjust the cut-out range 44La in the adjusted state indicated by a dotted line to the cut-out range 44La' indicated by a solid line.

In the case of the present modification, the coordinate extraction section 55al of FIG. 3 extracts coordinates (Xla1', Yla1') and (Xlb1', Ylb1') of the peaks of the contours of the illumination lens frames 21a1 and 21b1 in FIG. 7C.

However, the coordinates (Xlb1', Ylb1') are equivalent to the coordinates (Xlb1, Ylb1) in FIG. 7C. The cut-out range setting section 55a3 of FIG. 3 sets the new cut-out range 44La' including two coordinates (Xla1', Yla1') and (Xlb1', Ylb1') as peaks as shown in FIG. 7C. Note that in the case, the coordinates (X10, Y10) of the center are also changed to new coordinates (X10', Y10') (that are a point of intersection of the diagonals).

According to the present modification, each of the left and right cut-out ranges that substantially determines the characteristics of the three-dimensional view is set based on two reference positions, and each of the left and right cut-out ranges can be set more accurately than in the case of one reference position.

Note that in the present modification, predetermined ranges Lu1 and Lu2 may be set around coordinates (Xla1, Yla1) and (Xlb1, Ylb1) of positions that serve as references for determining the cut-out range 44La in the adjusted state as indicated by dotted lines in FIG. 7B, for example. Although the predetermined ranges Lu1 and Lu2 are circular regions around the coordinates (Xla1, Yla1) and (Xlb1, Ylb1) in FIG. 7B, the predetermined ranges Lu1 and Lu2 are not limited to the circular regions.

When the coordinates (Xla1', Yla1') and (Xlb1', Ylb1') of the peaks of the contours of the illumination lens frames 21a1 and 21b1 as the positions of two indexes to be picked up images at the adjustment exist in the predetermined ranges Lu1 and Lu2, conditions that can secure a predetermined performance by the adjustment based on the image processing are satisfied. When the coordinates (Xla1', Yla1') and (Xlb1', Ylb1') do not exist in the predetermined ranges Lu1 and Lu2, a warning may be issued.

This will be further described. The both image pickup sections 22L and 22R adjusted by the image processing are not in a mechanically (structurally) adjusted state, and it can be assumed that substantially the same performance as in the mechanically adjusted state can be realized when a relative deviation (from the horizontally symmetrical image pickup state) between the both image pickup sections 22L and 22R is in a small range.

However, when the relative deviation between the both image pickup sections 22L and 22R is large, the original performance facilitating the three-dimensional view that can be secured in the mechanically adjusted state may be reduced. For example, when a rotational deviation is generated in addition to a translational deviation, it may be difficult to secure the original performance by the adjustment of the cut-out range based on the image processing. Therefore, ranges of thresholds can be set for a case in which the original (adjusted) performance can be secured based on electrical adjustment by the adjustment unit 5 (adjustment based on image processing) and for a case in which it is better to perform the mechanical adjustment than to perform the electrical adjustment. A judgement result indicating whether the deviation is within the thresholds can be provided to the user, and this will be highly convenient for the user.

Therefore, in the present modification, the predetermined ranges Lu1 and Lu2 serving as the ranges of the thresholds that can secure the predetermined performance are checked in advance by the adjustment based on the image processing by the adjustment unit 5, and the predetermined ranges Lu1 and Lu2 are stored in the memory 56a. At the adjustment, the difference value calculation section 55a2 may calculate a difference value and may further judge whether the difference value exists in the predetermined ranges Lu1 and Lu2, for example. The difference value calculation section 55a2 may issue a warning to the user, such as an operator, if the difference value does not exist in the predetermined ranges Lu1 and Lu2. In this case, the difference value calculation section 55a2 functions as a judgement circuit or a judgement section configured to judge whether the position of the index at the adjustment exists in a range (or a predetermined range) of a threshold set near the reference position in the adjusted state.

Although FIG. 7B illustrates a case in which the predetermined ranges Lu1 and Lu2 are set on the left effective pixel region 43La side, a predetermined range may also be set on the right effective pixel region 43Ra side. In this case, the difference value calculation section 55a2 may also set the predetermined ranges in the case of FIG. 4A or FIG. 6B.

Figure 7D:
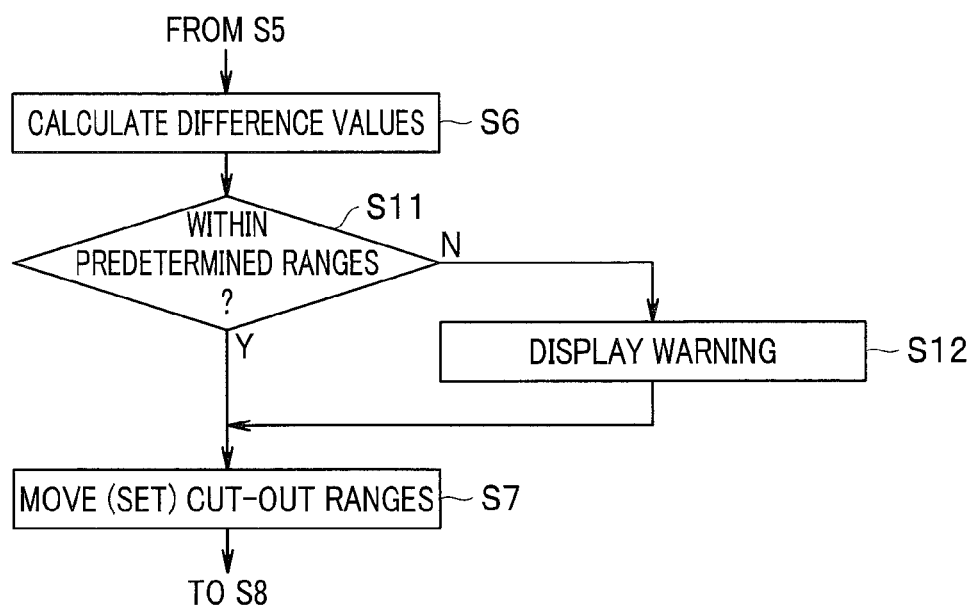
FIG. 7D is a flowchart showing part of a procedure of an adjustment process when an electrically permitted adjustment range is set.

FIG. 7D shows a process of part of the adjustment process when permissible ranges Lu1 and Lu2 are set in advance as in FIG. 7B. The process in the case is only partially different from FIG. 5, and the different part of the process will be described.

In the present modification, steps S1 to S6 of FIG. 5 are the same processes, and the description will be omitted (see FIG. 5). When the difference value calculation section 55a2 calculates difference values in step S6 for example, the difference value calculation section 55a2 judges whether the difference values exist in the predetermined ranges Lu1 and Lu2 in next step S11. If the difference values exist in the predetermined ranges, the process moves to step S7 as in the case of FIG. 5.

On the other hand, if the judgement result indicates that absolute values of the difference values do not exist in the predetermined ranges Lu1 and Lu2, the difference value calculation section 55a2 reads data for notification from the memory 56a and outputs the data for notification by superimposing the data on the image signal to be outputted toward the 3D mixer 6 side in step S12. The 3D monitor 7 then displays content for warning, for example. After the process of step S12, the process moves to step S7. In step S7 and subsequent steps, the processes are the same as in FIG. 5.

In the case of the present modification, the adjustment unit 5 forming the adjustment section includes, for example, the difference value calculation section 55a2 as a judgement circuit configured to judge whether the position data of the indexes whose images are picked up in the left and right peripheral side effective pixel regions at the adjustment instruction exists in the ranges (predetermined ranges Lu1 and Lu2) of the thresholds set in advance with respect to the reference position data of the indexes whose images are picked up in the left and right peripheral side effective pixel regions in the adjusted state. If the judgement result of the judgement circuit indicates that at least one of the left and right position data is out of the ranges of the thresholds, a warning is issued. That is, the difference value calculation section 55a2 forming the judgement circuit functions as a notification section (or a notification circuit) configured to notify the user such as a display for warning or the like.

In the case of the present modification, the user, such as an operator, can check the generation of a deviation in a level that it is better to perform mechanical adjustment, in at least one of the both image pickup sections 22L and 22R. The user can set the state for obtaining a predetermined performance by performing the mechanical adjustment before the next use of the stereoscopic endoscope 2, for example. According to the present modification, the state for obtaining the predetermined performance can be checked even in a state in which the stereoscopic endoscope 2 is repeatedly used for a long time, and timing for performing the mechanical adjustment can be recognized. Note that although the illumination lens frames 21a1 and 21b1 are used as the reference members in the description, the illumination lens 35 may be protruded from the distal end surface 15a, and the protruding illumination lens 35 may be used as the reference member.

Next, a third modification of the first embodiment will be described. In the description of the first embodiment, the both image pickup sections 22L and 22R are adjusted in advance to the horizontally symmetrical image pickup state and attached (fixed) to the distal end member 15b of the distal end portion 15.

On the other hand, in the present modification, an image pickup unit 71R including, for example, the right image pickup section 22R as one of the image pickup sections is inserted (housed), from the back side, into the right through hole 72R of the two image pickup unit through holes (simply called through holes) 72L and 72R separately provided in the horizontal direction in the distal end portion main body 15c as shown in FIG. 8. A rotation angle θRr around the optical axis Or is adjusted, and the image pickup unit 71R is attached (fixed). An image pickup unit 71L including the left image pickup section 22L as the other image pickup section is inserted (housed), from the back side, into the through hole 72L of the distal end portion main body 15c through a housing member 73L as an insertion member. A rotation angle θLr around the optical axis Ol and an inclination angle θLd of the optical axis Ol are adjusted to attach (fix) the image pickup unit 71L such that the image pickup unit 71L becomes horizontally symmetrical to the image pickup unit 71R. Note that the through holes 72L and 72R separated in the horizontal direction are provided in advance on the distal end portion main body 15c such that center axes become horizontally symmetrical.

As described below, the image pickup unit 71R in the state fitted to the through hole 72R abuts a tapered portion 77R and is positioned at a position along the optical axis Or direction. In the state that the rotation angle θRr around the optical axis Or is adjusted, the image pickup unit 71R is fixed to the distal end portion main body 15c by a screw, an adhesive 79R, or the like.

On the other hand, the through hole 72L can rotate the image pickup unit 71L about the optical axis Ol in a range of a predetermined angle, and the through hole 72L includes an air gap that allows fixing the image pickup unit 71L by slightly tilting the image pickup unit 71L from the direction of the optical axis Ol. As described below, the image pickup unit 71L is adjusted to be horizontally symmetrical to the image pickup unit 71R, and the image pickup unit 71L is fixed by a screw, an adhesive 79L, or the like.

The distal end member 15b in FIG. 8 includes: the distal end portion main body 15c provided with the through holes 72L and 72R; and the distal end cylindrical body 15d extending toward the back side of the distal end portion main body 15c and connected to the bending portion.

The image pickup unit 71R includes a connection portion 74R for connecting the CCD 24R and the cable 26b in the image pickup section 22R, and the image pickup unit 71L includes a connection portion 74L for connecting the CCD 24L and the cable 26a in the image pickup section 22L. Note that when sections including the connection portions 74L and 74R are defined as the image pickup sections 22L and 22R, respectively, the image pickup sections 22L and 22R are the same as the image pickup units 71L and 71R. Therefore, the content described for the image pickup units 71L and 71R can also be applied to the image pickup sections 22L and 22R.

In the image pickup section 22R of the image pickup unit 71R, the objective optical system 23R and the CCD 24R are attached to an image pickup section frame body 75R, and part of lenses of the objective optical system 23R is attached inside of the image pickup section frame body 75R through a lens frame 76R. The lens frame 76R is fixed to the image pickup section frame body 75R in a state that the position in the optical axis Or direction is adjusted, and the object at a predetermined distance is focused and the image is picked up on the image pickup surface of the CCD 24R.

The image pickup section frame body 75R of the image pickup unit 71R is inserted, from behind, into the through hole 72R in the distal end portion main body 15c and is fixed to the through hole 72R in a state that the image pickup section frame body 75R is positioned at the positioning tapered portion 77R. The image pickup section frame body 75R is fixed such that the direction of the optical axis Or of the image pickup unit 71R becomes a predetermined field of view direction Vr and is fixed by setting an azimuth in a circumferential direction of the image pickup unit 71R (rotation angle θRr about the optical axis Or) to a predetermined azimuth (that is, fixed in a state that the inclination is eliminated).

The image pickup unit 71L has the same configuration as the image pickup unit 71R, and the description will be omitted. However, an image pickup section frame body 75L is covered by the housing member 73L in the image pickup unit 71L, and the housing member 73L can be inserted into the through hole 72L to adjust and attach the image pickup unit 71L. Therefore, the through hole 72L is set to a size that allows loosely fit and house the housing member 73L, and the inclination angle θLd of the optical axis Ol and the azimuth θLr in the circumferential direction of the image pickup unit 71L (azimuth or rotation angle about the optical axis Ol) can be adjusted (in a predetermined range) at a positioning tapered portion 77L.

As described in the first embodiment, the images of the index 25b picked up in the effective pixel regions 43La and 43Ra of the both CCDs 24L and 24R are used to perform an adjustment as follows.

The image of the index 25b picked up in the effective pixel region 43Ra of the CCD 24R is displayed on the 3D monitor 7 to check the position of the index 25b. In this case, an image in a state close to the state shown on the right side of FIG. 4A is obtained. The coordinates (Xr1, Yr1) of the position of the index 25b in this case are set as reference coordinates, and the cut-out range 44Ra is set based on the coordinates (Xr1, Yr1). The data of the coordinates (Xr1, Yr1) and the cut-out range 44Ra are stored in the memory 56b.

The image of the index 25b picked up in the effective pixel region 43La of the CCD 24L is displayed on the 3D monitor 7, and the inclination angle θLd and the rotation angle θLr of the image pickup unit 71L are adjusted. The inclination angle θLd is adjusted to adjust the field of view direction Vl that is the direction of the optical axis Ol, such that the field of view direction Vl becomes horizontally symmetrical to the field of view direction Vr of the optical axis Or. As a result of the adjustment, the center positions in picking up an image at the point P0 (point corresponding to the point P0) at the predetermined distance L from the distal end surface 15a can be set to coincide on both images as shown in FIG. 4C.

The rotation angle θLr can be adjusted in the image of the index 25b picked up in the effective pixel region 43La of the CCD 24L such that the position of the index 25b becomes horizontally symmetrical with respect to the image of the index 25b picked up in the effective pixel region 43Ra of the CCD 24R, and a state without inclination (with respect to the rotation angle of the CCD 24R) can be set. The coordinates (Xl1, Yl1) of the position of the index 25b after the adjustment are set as the reference coordinates, and the cut-out range 44La is set based on the coordinates (Xl1, Yl1). Data of the coordinates (Xl1, Yl1) and the cut-out range 44La is stored in the memory 56a.

In the case of the present modification, the endoscope distal end portion includes the left and right through holes 72L and 72R for separately housing the first image pickup section and the second image pickup section in the horizontal direction in the columnar distal end portion main body 15c included in the endoscope distal end portion. One through hole of the left and right through holes 72L and 72R houses one image pickup section of the first image pickup section and the second image pickup section such that the one image pickup section can rotate by at least a predetermined angle about the optical axis of the one image pickup section. The other through hole of the left and right through holes 72L and 72R houses the other image pickup section of the first image pickup section and the second image pickup section such that the other image pickup section can rotate by at least a predetermined angle about the optical axis of the other image pickup section and such that the inclination of the other image pickup section in the optical axis direction can be adjusted. The adjustment section configured to adjust at least one image pickup section of the first image pickup section and the second image pickup section adjusts the rotation angle of the one image pickup section about the optical axis direction to fix the one image pickup section to the one through hole and adjusts the rotation angle of the other image pickup section about the optical axis of the other image pickup section and the inclination of the optical axis to fix the other image pickup section to the other through hole such that one image of a first image and a second image of the index member 25 as a reference member picked up by the first image pickup section and the second image pickup section becomes horizontally symmetrical to the other image of the first image and the second image.

According to the present modification, the frame body of one image pickup section (more specifically, 22R) or image pickup unit (more specifically, 71R) is fixed in the through hole 72R in the distal end portion main body 15c at the rotation angle θRr about the optical axis Or, and the inclination angle θLd of the optical axis Ol and the rotation angle θLr are adjusted to fix (attach) the other image pickup section 22L or image pickup unit 71L to the through hole 72L in the distal end portion main body 15c in the state that the other image pickup section 22L or image pickup unit 71L becomes horizontally symmetrical to the image pickup section 22R or the image pickup unit 71R. Therefore, the diameter of the distal end portion 15 can be smaller than in a structure in which both are adjusted and fixed, and the adjustment is easier than in the case in which both are adjusted and fixed. Note that in FIG. 8, the image pickup unit 71L is fixed to the through hole 72L in the state that the image pickup unit 71L is covered by the housing member 73L, by adjusting the image pickup unit 71L such that the image pickup unit 71L becomes horizontally symmetrical to the other image pickup unit 71R. However, instead of using the housing member 73L, the size of the through hole 72L may be slightly larger than the size in the state in which the through hole 72L is fitted to the image pickup unit 71L, and the inclination angle θLd of the optical axis Ol and the rotation angle θLr of the image pickup unit 71L side may be adjusted to fix the image pickup unit 71L.

Second Embodiment

Figure 9:
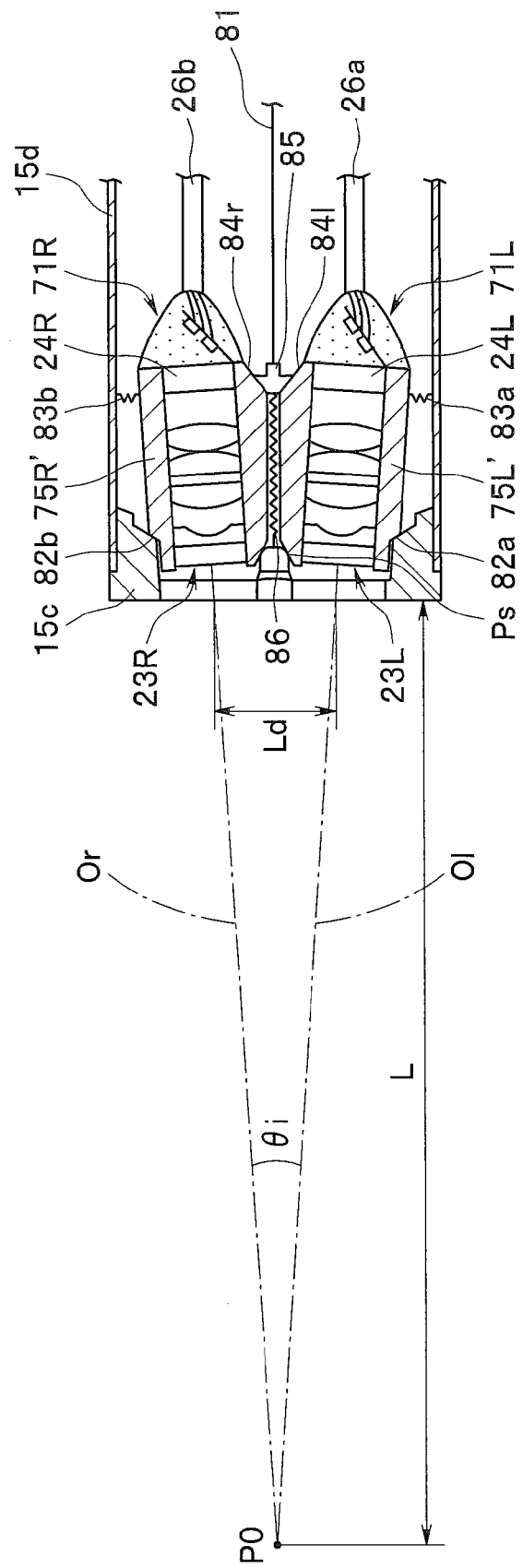
FIG. 9 is a cross-sectional view showing a schematic configuration of the distal end portion of the stereoscopic endoscope according to a second embodiment of the present invention.

Next, a second embodiment of the present invention will be described. FIG. 9 shows a configuration of the distal end portion 15 in the stereoscopic endoscope 2 (see FIG. 10) according to the present embodiment. Note that the light source apparatus 3, the CCUs 4A and 4B, the adjustment unit 5, the 3D mixer 6, and the 3D monitor 7 other than the stereoscopic endoscope 2 are the same as in the first embodiment.

In the present embodiment, the both image pickup units (or image pickup sections) 71L and 71R mounted in the distal end portion 15 have a structure, in which a wire 81 as a pulling member is pulled by a hand side pulling operation object on a hand side that can be pulled and operated, and an inward angle θi as an angle formed by the both optical axes Ol and Or or an angle formed by the both field of view directions Vl and Vr is variable.

Note that the distal end portion 15 is provided with, for example, the illumination lens frames 21a1 and 21b1 as shown in FIG. 6 as index members forming reference members described in the first embodiment.

Before the factory shipment for example, an adjustment for eliminating off-center of the both image pickup units (or image pickup sections) 71L and 71R, an adjustment for making inclination angles θd of the both optical axes Ol and Or equal to each other, and an adjustment of rotation angles θr of the both optical axes Ol and Or are performed for one or more representative values of the inward angle θi. An adjustment is also performed to make the both field of view directions Vl and Vr horizontally symmetrical. For one or more representative values of the inward angle θi, the cut-out ranges can be set by the adjustment unit 5 as described in the first embodiment.

Distal end sides of the both image pickup units 71L and 71R are supported by tapered portions 82a and 82b of the through holes of the distal end portion main body 15c included in the distal end portion 15, and rear end sides of the image pickup units 71L and 71R are urged inside by elastic force of springs 83a and 83b, respectively, on planes including the optical axes Ol and Or.

Tapered notch portions 84r and 84l are formed on rear end sides of frame bodies 75L' and 75R' holding the objective optical systems 23L and 23R and the CCDs 24L and 24R in the image pickup units 71L and 71R. A trapezoidal abutment member 85 abuts the notch portions 84r and 84l, and the abutment member 85 is urged such that elastic force pulls the abutment member 85 toward a support member on the distal end side through a spring 86.

Note that the wire 81 may be slightly slackened according to a case in which the insertion portion 11 is inserted into a bent site or the like. In such a case, the slackening is eliminated by the elastic force of the spring 86, and the abutment member 85 is brought into contact with the notch portions 84r and 84l to set a state of the predetermined inward angle θi. However, a structure without the spring 86 is possible if the slacking can be ignored.

The image pickup unit 71R shown in FIG. 9 is simply illustrated, in which, for example, the connection portion 74R part is reshaped into a connection portion provided with electronic components in the image pickup unit 71R of FIG. 8, and the image pickup section frame body 75R and the lens frame body 76R are collectively expressed by a frame body 75R'. The image pickup unit 71L shown in FIG. 9 also has the same configuration. Note that the distal end portion 15c is sealed by another frame member (not shown) and a cover glass (not shown), and water tightness is maintained.

The elastic force of the springs 83a and 83b and the elastic force of the spring 86 for urging the abutment member 85 to the distal end side usually put the both image pickup units 71L and 71R into a state in which the inward angle θi is a largest angle as shown in FIG. 9.

Figure 10:
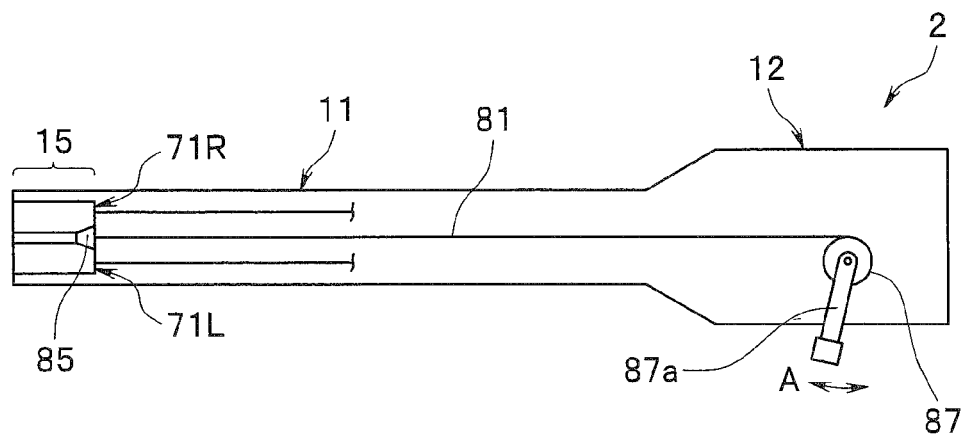
FIG. 10 is a diagram showing a schematic configuration of the stereoscopic endoscope according to the second embodiment.

The wire 81 is inserted into the insertion portion 11 as shown in a schematic diagram of FIG. 10, and a rear end of the wire 81 is wound around and attached to a pulley 87 in the operation portion 12 on the hand side of the stereoscopic endoscope 2. The pulley 87 is provided with a knob 87a as a hand side pulling operation object for rotating the pulley 87 to pull the wire 81, and the user can perform operation of rotating the knob 87a to change the inward angle θi.

In this case, the image pickup units 71R and 71L shown in FIG. 9 are movable relative to the distal end portion 15c. Therefore, the distance L between the point of intersection P0 of the both optical axes Ol and Or and the distal end surface and a distance (or optical axis interval) Ld between the optical axes of the image pickup units 71R and 71L on the distal end surface are changed to change the inward angle θi. Note that the distance (or optical axis interval) Ld between the optical axes of the image pickup units 71R and 71L on the distal end surface can also be called an interval between the both field of view directions Vl and Vr on the distal end surface.

Figure 11:
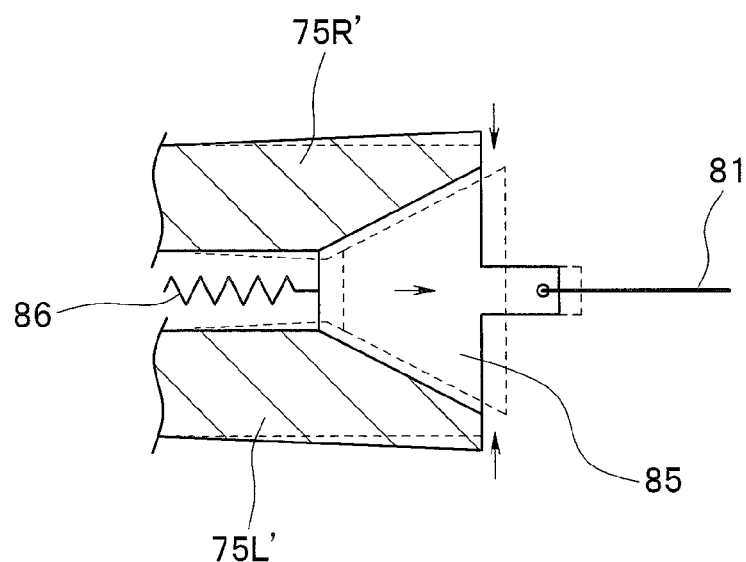
FIG. 11 is an enlarged view of the vicinity of an abutment member for changing an inward angle.

For example, when the knob 87a of FIG. 10 is rotated clockwise (direction toward reference sign A side in FIG. 10) to perform operation of pulling the wire 81 to the hand side, the abutment member 85 moves toward the back side as indicated by a dotted line in FIG. 11. As a result of the movement of the abutment member 85, the elastic force of the springs 83a and 83b rotates and moves the back side parts of the frame bodies 75L' and 75R' inside, with positions on the distal end side (positions supported by the tapered portions 82a and 82b) as fulcrums. In this case, the distance L between the point of intersection P0 of the optical axes Ol and Or of the image pickup units 71L and 71R and the distal end surface becomes long. The optical axis interval Ld becomes narrow due to a distance between the distal end surface and a contact point Ps of the image pickup units 71L and 71R and the distal end portion 15c, and the inward angle θi becomes small. The field of view directions Vl and Vr also change. That is, when the knob 87a is rotated clockwise to pull the wire 81 to increase the amount of movement of the abutment member 85, the inward angle θi can be reduced.

Conversely, when the knob 87a is rotated counterclockwise, the optical axes Ol and Or of the image pickup units 71L and 71R change due to the urging force of the spring 86, and the distance L between the point of intersection P0 and the distal end surface becomes short. The optical axis interval Ld becomes wide due to the distance between the distal end surface and the contact point Ps of the image pickup units 71L and 71R and the distal end portion 15c, and the inward angle θi can be increased.

According to the present embodiment, the inward angle θi can be changed by the operation portion 12 on the hand side, and the inward angle θi desired by the subject to be observed or the operator can be set for the three-dimensional view.

Figure 12:
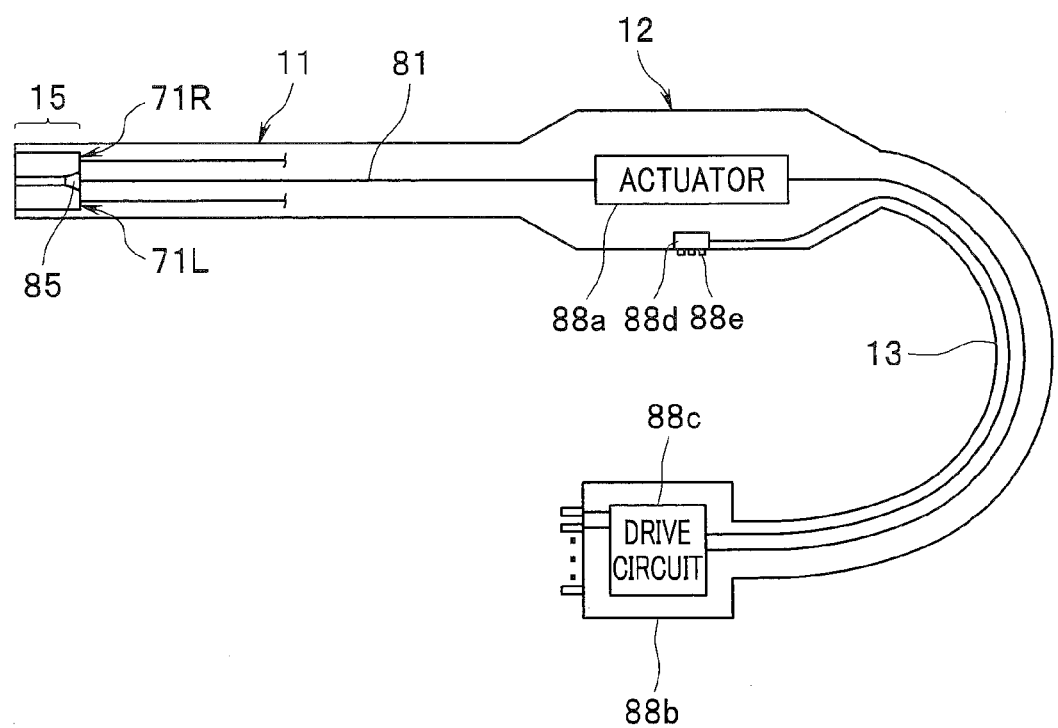
FIG. 12 is a diagram showing a schematic configuration of the stereoscopic endoscope according to a first modification of the second embodiment.

Although the wire 81 is pulled by manual operation to change the inward angle θi in the structure described above, the wire 81 may be electrically driven as in a following first modification. FIG. 12 shows a schematic configuration of the stereoscopic endoscope 2 in this case.

An actuator 88a configured to move the wire 81 in a longitudinal direction of the wire 81 is provided inside of the operation portion 12, and a drive circuit 88c configured to drive the actuator 88a is housed in one connector 88b of connectors (the other connector is not shown) provided on the end portion of the universal cable 13. The operation portion 12 is also provided with a switching circuit 88d configured to perform operation of changing the inward angle θi, and based on a signal of the switching circuit 88d, the drive circuit 88c applies a drive signal for driving the actuator 88a to the actuator 88a.

Note that the connector 88b is connected to the CCU 4A or 4B. The switching circuit 88d includes a plurality of switches 88e provided on the operation portion 12. The strength of the drive signal varies according to the operated switch, and the amount of movement for pulling the wire 81 varies. According to the present modification, the inward angle θi can be changed by the switch operation. In addition, the present modification has the same effects as in the second embodiment.

Although the inward angle θi is changed by changing the directions of the optical axes Ol and Or of the two both image pickup units (or image pickup sections) 71L and 71R such that the directions become horizontally symmetrical in the configuration described in the second embodiment, the inward angle θi may be changed by changing the direction of the optical axis of only one of the both image pickup units (or image pickup sections) (that is, one of the field of view directions) as in a second modification described below.

Figure 13:
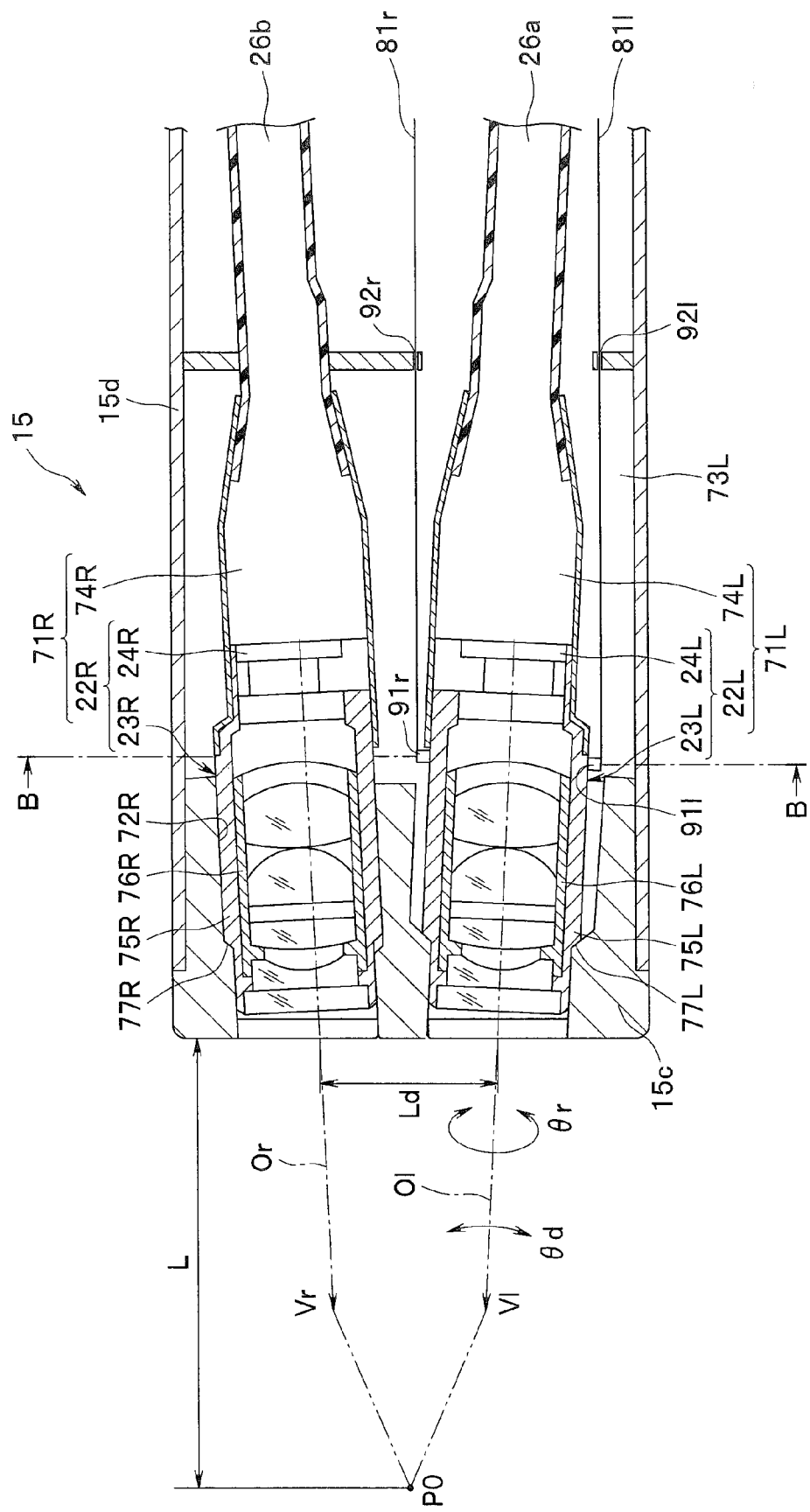
FIG. 13 is a cross-sectional view showing a schematic configuration of the distal end portion of the stereoscopic endoscope according to a second modification of the second embodiment.
Figure 14:
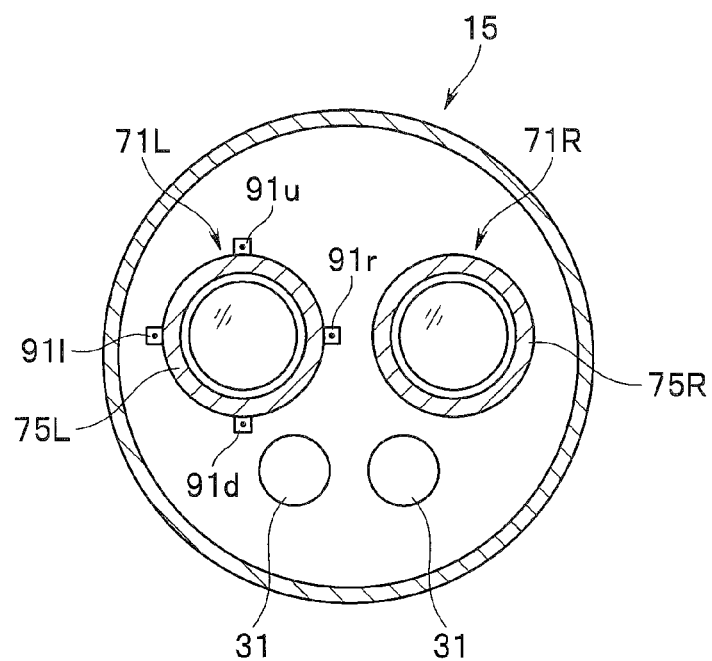
FIG. 14 is a B-B line cross-sectional view of FIG. 13.

FIG. 13 shows a configuration of the distal end portion 15 according to the second modification, and FIG. 14 shows a B-B cross-sectional view of FIG. 13.

As shown in FIG. 13, one image pickup unit 71R of the image pickup units is fixed to the distal end portion main body 15c like the one shown in FIG. 8.

On the other hand, the other image pickup unit 71L abuts the tapered portion 77L of the distal end portion main body 15c and is supported such that the optical axis Ol direction can be changed. The image pickup section frame body 75L of the image pickup unit 71L is provided with wire attachment portions 91u, 91d, 91l, and 91r for attaching distal ends of wires 81u, 81d, 81l, and 81r at vertical and horizontal positions on the outer circumferential face, at positions on the back side of the tapered portion 77L.

Note that FIG. 13 shows two wires 81l and 81r and two wire attachment portions 91l and 91r, and FIG. 14 shows the wire attachment portions 91u, 91d, 91l, and 91r at four parts.

As shown in FIG. 13, wire receivers 92u, 92d, 92l, and 92r for restricting the expansion of the wires 81u, 81d, 81l, and 81r to the center side closer to the optical axis Ol are provided at positions on the back side of the wire attachment portions 91u, 91d, 91l, and 91r in the distal end portion 15. Note that in the example shown in FIG. 13, the wire receivers 92u, 92d, 92l, and 92r are formed by providing through holes in a wire receiving member 92.

The rear end side of the wires 81u, 81d, 81l, and 81r having passed through the wire receivers 92u, 92d, 92l, and 92r, respectively, is wound around the pulley 87 as shown in FIG. 10, for example. In this case, the wires 81u and 81d are wound around one pulley (87a, although not shown) from directions opposite to each other, and the wires 81l and 81r are wound around another pulley (87b, although not shown) from directions opposite to each other.

The pulleys 87a and 87b are connected to two knobs not shown, and the pulley 87a or 87b is rotated by rotation operation of the knob, and one of the wires 81u and 81d as pulling members or one of the wires 81l and 81r is pulled. The direction of the optical axis Ol of the image pickup unit 71L can be changed to the pulled side.

For example, when the pulley 87a is rotated and operated to pull the wire 81l to the hand side for example, force for rotating the rear end side of the image pickup unit 71L to the center axis side of the distal end portion 15 acts on the image pickup unit 71L with the tapered portion 77L as a fulcrum. The optical axis Ol changes relative to the optical axis Or. The distance L between the point of intersection P0 of the optical axis Or and the optical axis Ol and the distal end surface becomes long, and the distance Ld between optical axes of the optical axis Or and the optical axis Ol becomes short. Therefore, the inward angle θi becomes small.

When the wire 81r is operated to pull the wire 81r to the hand side, the optical axis Ol changes relative to the optical axis Or, and the distance L between the point of intersection P0 of the optical axis Or and the optical axis Ol and the distal end surface becomes short, and the distance Ld between optical axes of the optical axis Or and the optical axis Ol becomes short. Therefore, the inward angle θi becomes large.

In the present modification, the inward angle can be changed by the operation on the hand side. In addition to changing the inward angle, the direction of the optical axis Ol, that is, the field of view direction Vl can also be changed to a direction perpendicular to the horizontal surface including the both optical axes Ol and Or.

Figure 15:
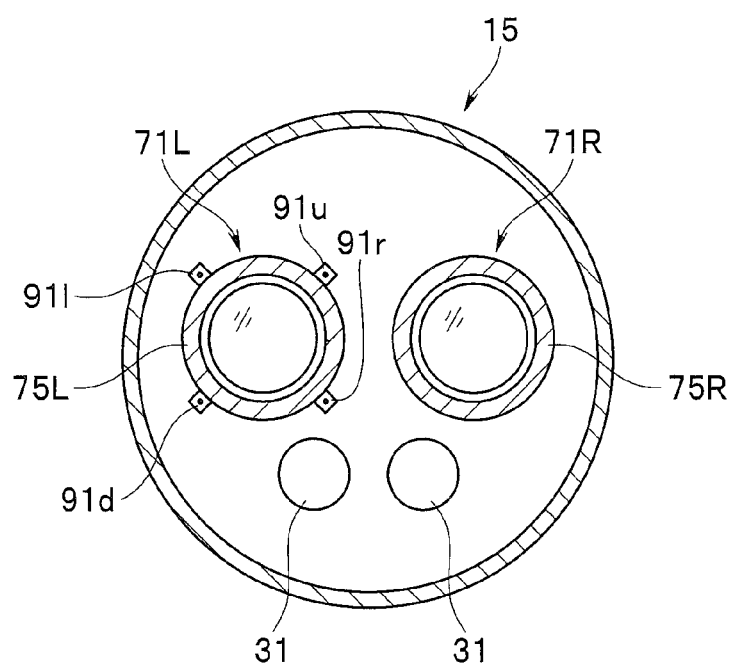
FIG. 15 is a cross-sectional view showing a schematic configuration of the distal end portion of the stereoscopic endoscope according to a third modification of the second embodiment.

As in a third modification shown in FIG. 15, the direction (azimuth) (around the optical axis) of providing the wire attachment portions 91u, 91d, 91l, and 91r may be changed. In FIG. 15, the direction of providing the wire attachment portions 91u, 91d, 91l, and 91r is changed to, for example, positions rotated about 45 degrees from the configuration of FIG. 14.

According to the configuration, a space for more widely changing the optical axis Ol direction of the image pickup unit 71L in the distal end portion 15 can be secured. In other words, when the same change range as in FIG. 14 is secured, the outer diameter of the distal end portion 15 can be reduced.

Note that although the wire attachment portions 91l and 91r for attaching (fixing) the distal ends of the wires 81u, 81d, 81l, and 81r for changing or adjusting the direction of the optical axis Ol are provided on the outer circumferential face of the image pickup section frame body 75L in the present modification, a ring (will be called an adjustment ring) provided with the wire attachment portions 91u, 91d, 91l, and 91r may be provided on the outer circumferential face of the image pickup section frame body 75L.

Figure 16:
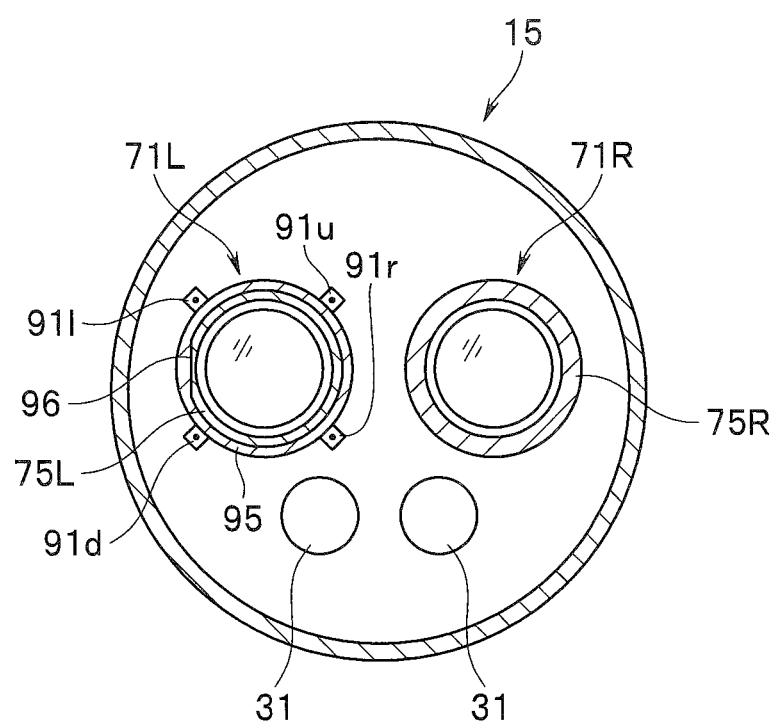
FIG. 16 is a cross-sectional view showing a schematic configuration of the distal end portion of the stereoscopic endoscope according to a fourth modification of the second embodiment.

A fourth modification shown in FIG. 16 shows a case in which an adjustment ring 95 is used. As shown in FIG. 16, the thickness of the image pickup section frame body 75L is reduced, and the adjustment ring 95 provided with the wire attachment portions 91u, 91d, 91l, and 91r is provided on the outer circumferential face of the image pickup section frame body 75L. A D-cut portion 96 is also provided in a predetermined direction on the image pickup section frame body 75L to facilitate the positioning in the circumferential direction in attaching the adjustment ring 95 to the image pickup section frame body 75L, and the adjustment ring 95 is shaped to suit the D-cut portion 96.

Note that when the image pickup sections 22L and 22R or the image pickup units 77L and 77R are to be adjusted in the first embodiment, the second embodiment, or the like, the vertical and horizontal directions of the image pickup sections 22L and 22R or the image pickup units 77L and 77R may be hard to recognize if the diameter of the distal end portion 15 is small. In such a case, for example, direction index data may be stored in advance in the memories 56a and 56b in the adjustment unit 5 of FIG. 3 to display direction indexes indicating an upward direction and a left direction when images of the effective pixel regions 43La and 43Ra are displayed.

When instruction operation for displaying the direction indexes is performed, a direction index 94a of the upward direction and a direction index 94b of the left direction may be displayed as indicated by, for example, dotted lines in FIG. 4C to allow easily recognizing the vertical and horizontal directions of the image pickup sections 22L and 22R and the image pickup units 77L and 77R.

Embodiments formed by partially combining the embodiments described above including the modifications also belong to the present invention.

What is claimed is:

1. A stereoscopic endoscope system comprising:
 a first image pickup section provided on an endoscope distal end portion, having a first field of view direction, and comprising a first objective optical system and a first image pickup device configured to acquire a first image of a subject;
 a second image pickup section provided on the endoscope distal end portion separately from the first image pickup section in a horizontal direction, having a second field of view direction, and comprising a second objective optical system and a second image pickup device configured to acquire a second image of the subject;
 a reference member integrally provided on the endoscope distal end portion and serving as a reference in adjusting the first and second image pickup sections such that images of at least a distal end side are picked up in first and second image pickup ranges that can be picked up by the first and second image pickup devices, respectively; and an adjustment section configured to adjust the image picked up by at least one of the image pickup sections or configured to adjust the one of the image pickup sections to generate substantially horizontally symmetrical images when the first image and the second image obtained by picking up the images of the reference member by the first and second image pickup devices, respectively, are displayed as left and right images in a display region of a display apparatus.

2. The stereoscopic endoscope system according to claim 1, wherein the reference member is provided on a distal end surface of the endoscope distal end portion to protrude from the distal end surface, images of an index on a distal end side of the reference member are picked up only in regions on peripheral sides in the first and second image pickup ranges, and the index is provided at a predetermined position on the distal end surface such that the index becomes horizontally symmetrical in the first and second image pickup ranges.

3. The stereoscopic endoscope system according to claim 2, wherein the adjustment section comprises: a cut-out range setting circuit configured to remove left and right peripheral side effective pixel regions that are the peripheral sides in the first and second image pickup ranges in which the images of the index of the reference member are picked up, from left and right effective pixel regions forming the first and second image pickup ranges, respectively, to cut out left and right center side effective pixel regions; and an enlargement circuit configured to execute an enlargement process to display images picked up in the center side effective pixel regions cut out by the cut-out range setting circuit as left and right images on an entire display region of the display apparatus.

4. The stereoscopic endoscope system according to claim 3, wherein the adjustment section further comprises a reference data storage section configured to store, in advance, position data of the images of the index picked up in the left and right peripheral side effective pixel regions, respectively, as left and right reference position data in an adjusted state in which the first and second image pickup sections are adjusted to a horizontally symmetrical image pickup state, the cut-out range setting circuit uses the left and right reference position data in the adjusted state stored in the reference data storage section to set in advance the left and right cut-out ranges that serve as references, and the reference data storage section stores data for determining the left and right cut-out ranges that serve as the references along with the reference position data.

5. The stereoscopic endoscope system according to claim 4, wherein the adjustment section further comprises a difference value calculation circuit configured to calculate difference values between the left and right position data of the images of the index respectively picked up in the left and right peripheral side effective pixel regions and the left and right reference position data of the images of the index respectively picked up in the adjusted state stored in the reference data storage section when an adjustment instruction is issued to the adjustment section, and the cut-out range setting circuit shifts the left and right cut-out ranges in the adjusted state by amounts equivalent to the difference values calculated by the difference value calculation circuit to set new cut-out ranges upon the adjustment instruction.

6. The stereoscopic endoscope system according to claim 5, wherein the adjustment section further comprises: a judgement circuit configured to judge whether the left and right position data of the images of the index picked up in the left and right peripheral side effective pixel regions upon the adjustment instruction exists in a range of a threshold set in advance, with respect to the left and right reference position data of the images of the index picked up in the left and right peripheral side effective pixel regions in the adjusted state; and a notification circuit configured to issue a warning if a judgement result of the judgement circuit indicates that at least one of the left and right position data is out of the range of the threshold.

7. The stereoscopic endoscope system according to claim 1, wherein the endoscope distal end portion comprises left and right through holes for housing the first image pickup section and the second image pickup section separately in the horizontal direction, one through hole of the left and right through holes houses one image pickup section of the first image pickup section and the second image pickup section such that the one image pickup section can rotate by at least a predetermined angle about an optical axis of the one image pickup section, another through hole of the left and right through holes houses another image pickup section of the first image pickup section and the second image pickup section such that the other image pickup section can rotate by at least a predetermined angle about an optical axis of the other image pickup section and such that an inclination of the optical axis of the other image pickup section can be adjusted, and the adjustment section adjusts a rotation angle of the one image pickup section about the optical axis to fix the one image pickup section to the one through hole and adjusts a rotation angle of the other image pickup section about the optical axis and the inclination of the optical axis to fix the other image pickup section to the other through hole such that one image of the first image and the second image and another image of the first image and the second image become horizontally symmetrical when respective images of the reference member are picked up.

8. The stereoscopic endoscope system according to claim 2, wherein the endoscope distal end portion comprises left and right through holes for housing the first image pickup section and the second image pickup section separately in the horizontal direction, one through hole of the left and right through holes houses one image pickup section of the first image pickup section and the second image pickup section such that the one image pickup section can rotate by at least a predetermined angle about an optical axis of the one image pickup section, another through hole of the left and right through holes houses another image pickup section of the first image pickup section and the second image pickup section such that the other image pickup section can rotate by at least a predetermined angle about an optical axis of the other image pickup section and such that an inclination of the optical axis of the other image pickup section can be adjusted, and the adjustment section adjusts a rotation angle of the one image pickup section about the optical axis to fix the one image pickup section to the one through hole and adjusts a rotation angle of the other image pickup section about the optical axis and the inclination of the optical axis to fix the other image pickup section to the other through hole such that one image of the first image and the second image and another image of the first image and the second image become horizontally symmetrical when respective images of the index are picked up.

9. The stereoscopic endoscope system according to claim 2, wherein the reference member is formed by illumination lenses or illumination lens frames provided with the illumination lenses, the illumination lenses arranged on peripheries of the first image pickup section and the second image pickup section in the endoscope distal end portion to protrude from the distal end surface and configured to emit illuminating light, and positions of contours of images of distal end sides in the illumination lenses or the illumination lens frames picked up in the left and right peripheral side effective image pickup regions are set as the index.

10. The stereoscopic endoscope system according to claim 5, further comprising:

a pulling member configured to work in conjunction with at least one image pickup section of the first image pickup section and the second image pickup section and capable of changing at least one of the field of view directions; an urging member configured to urge the at least one image pickup section toward the endoscope distal end portion; and a hand side operation object capable of pulling operation of the pulling member.

11. The stereoscopic endoscope system according to claim 10, wherein the pulling member and the at least one image pickup section are further provided with a contact point of the at least one image pickup section and the endoscope distal end portion, the urging member for urging toward the endoscope distal end portion, and the pulling member to allow changing an inward angle by changing a distance between a point of intersection of the first field of view direction and the second field of view direction and an endoscope distal end surface and by changing an interval between the first field of view direction and the second field of view direction.

12. The stereoscopic endoscope system according to claim 2, wherein the reference member comprises two indexes, images of the two indexes are picked up only in regions of the peripheral sides in the first and second image pickup ranges, respectively, and the two indexes are provided at predetermined positions on the distal end surface such that the two indexes become horizontally symmetrical in the first and second image pickup ranges.

13. The stereoscopic endoscope system according to claim 3, wherein the stereoscopic endoscope system comprises: a stereoscopic endoscope comprising the first image pickup section and the second image pickup section; and an image processing apparatus configured to execute image processing for the first image pickup section and the second image pickup section, and the image processing apparatus comprises the cut-out range setting circuit and the enlargement circuit.

* * * * *